(12) United States Patent
Sano et al.

(10) Patent No.: US 11,702,650 B2
(45) Date of Patent: Jul. 18, 2023

(54) CHROMATOGRAPHIC TEST DEVICE

(71) Applicant: KANEKA CORPORATION, Osaka (JP)

(72) Inventors: Sotaro Sano, Hyogo (JP); Shigehiko Miyamoto, Hyogo (JP); Takaaki Jikihara, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 478 days.

(21) Appl. No.: 16/870,104

(22) Filed: May 8, 2020

(65) Prior Publication Data
US 2020/0263164 A1  Aug. 20, 2020

Related U.S. Application Data

(63) Continuation of application No. PCT/JP2018/041284, filed on Nov. 7, 2018.

(30) Foreign Application Priority Data

Nov. 8, 2017 (JP) .................................. 2017-215975
Nov. 8, 2017 (JP) .................................. 2017-215977
Nov. 8, 2017 (JP) .................................. 2017-215984

(51) Int. Cl.
*C12N 15/10* (2006.01)
*B01D 15/22* (2006.01)
(Continued)

(52) U.S. Cl.
CPC ........... *C12N 15/101* (2013.01); *B01D 15/22* (2013.01); *B01D 15/3819* (2013.01); *G01N 30/16* (2013.01); *G01N 30/6047* (2013.01)

(58) Field of Classification Search
CPC .... B01L 3/50; B01L 3/508; B01L 3/52; B01L 3/56; B01L 2300/0672; G01N 33/4875; G01N 33/48778; A47J 31/0673
See application file for complete search history.

(56) References Cited

U.S. PATENT DOCUMENTS

| 6,634,243 | B1 | 10/2003 | Wickstead et al. |
| 2009/0181388 | A1* | 7/2009 | You ...................... C12Q 1/6848 435/287.2 |

(Continued)

FOREIGN PATENT DOCUMENTS

| JP | 2005515431 A | 5/2005 |
| JP | 2009216651 A | 9/2009 |

(Continued)

OTHER PUBLICATIONS

Extended European Search Report issued in corresponding European Patent Application No. 18875882.5, dated Jul. 16, 2021 (9 pages).

(Continued)

*Primary Examiner* — Ryan B Huang
(74) *Attorney, Agent, or Firm* — Osha Bergman Watanabe & Burton LLP

(57) ABSTRACT

A test device is provided that can comprise: a housing accommodating a chromatography support, wherein the housing comprises: a supporting part that supports a container accommodating a liquid used for chromatography. A method is provided for performing chromatography using the test device.

12 Claims, 36 Drawing Sheets

(51) Int. Cl.
*B01D 15/38* (2006.01)
*G01N 30/16* (2006.01)
*G01N 30/60* (2006.01)

(56) References Cited

U.S. PATENT DOCUMENTS

| | | |
|---|---|---|
| 2010/0285454 A1 | 11/2010 | You et al. |
| 2012/0034140 A1 | 2/2012 | Ohmiya et al. |
| 2015/0050720 A1 | 2/2015 | Mendoza Montero et al. |
| 2017/0153232 A1 | 6/2017 | Zhu |

FOREIGN PATENT DOCUMENTS

| | | |
|---|---|---|
| JP | 2010500009 A | 1/2010 |
| JP | 2015512250 A | 4/2015 |
| WO | 2010116979 A1 | 10/2010 |
| WO | 2014000037 A1 | 1/2014 |
| WO | 2017/130780 A1 | 8/2017 |

OTHER PUBLICATIONS

International Search Report issued in corresponding International Application No. PCT/JP2018/041284, dated Feb. 5, 2019 (2 pages).
Written Opinion issued in corresponding International Application No. PCT/JP2018/041284, dated Feb. 5, 2019 (7 pages).
Office Action issued in corresponding Japanese Patent Application No. JP 2018-209322 A; dated Sep. 6, 2022 (7 pages).

* cited by examiner

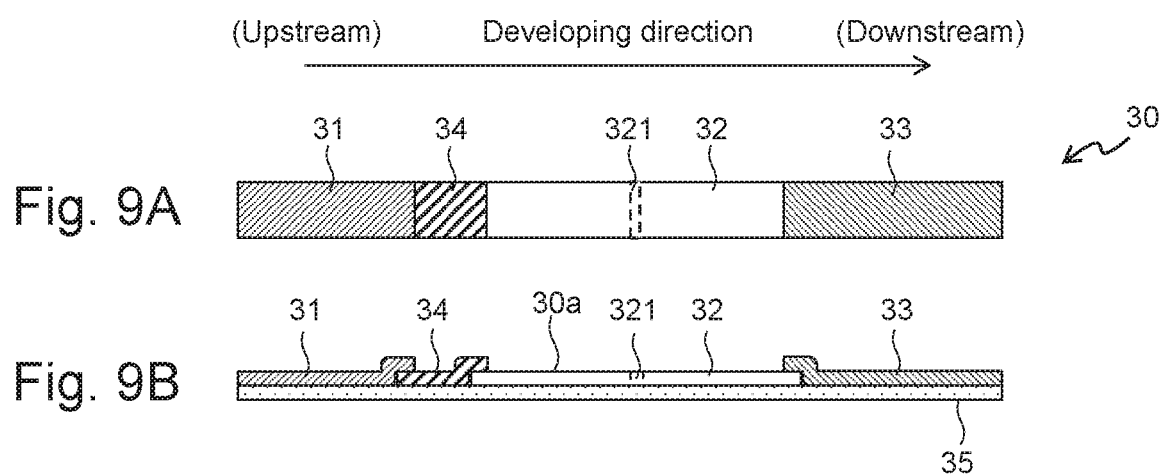

CHROMATOGRAPHIC TEST DEVICE

TECHNICAL FIELD

One or more embodiments of the present invention relates to a test device used for chromatography.

BACKGROUND

Nucleic acid chromatography is carried out on a chromatography support comprising a nucleic acid immobilized thereon to develop, capture, and detect a detection target comprising a nucleic acid tag hybridizing to the nucleic acid immobilized on the support. Nucleic acids comprising different nucleotide sequences are immobilized on a chromatography support at different positions, and each of a plurality of detection targets is tagged with a nucleic acid tag specific to the nucleic acid, so that a plurality of detection targets contained in a single specimen can be detected on a single support. In addition to nucleic acid chromatography, techniques of chromatography comprising capturing the detection targets on a chromatography support with the use of an antigen-antibody combination or a ligand-receptor combination capable of forming a specific bond are extensively used in the field of, for example, molecular biological testing or genetic testing for medical or food testing.

The chromatography techniques as described above involve the use of various types of liquids, such as a sample liquid containing detection targets or developing liquids. When such liquids are removed from a container with the use of an instrument, such as a pipette, and applied to a chromatography support, the liquid may disperse in the testing environment and contaminate the environment, which may lead to a false-positive result. By opening the container in the test environment, a liquid in the container may be contaminated.

An apparatus that breaks a part of a container to allow a liquid to leak therefrom and brings the leaked liquid into contact with a chromatography support while maintaining a liquid, such as a sample liquid or developing liquid, used for chromatography inside the container without the use of an instrument, such as a pipette, has been developed.

For example, a device for detection of analytes in affinity bioassays disclosed in Patent Document 1 comprises at least one transparent wall, at least one test recess adapted to receive at least one test strip and arranged in a manner such that said test strip is visible through the transparent wall, at least one cavity adapted to receive a container accommodating a fluid sample, said cavity being in fluid communication with said at least one test recess, and piercing means arranged in correspondence with said at least one cavity, in a manner such that, upon insertion of a container in the cavity, the container is pierced and at least an area of the sample is released from the container and reaches the test recess.

Also, a totally-enclosed device for quick detection of a target nucleic acid amplification product disclosed in Patent Document 2 comprises an inner core and an outer casing, wherein the inner core comprises a fixing case part and a base part, the fixing case part being provided with two holes respectively for housing washing buffer vacuoles and a PCR tube containing an amplification product, the base part comprising a washing buffer container element having a vacuole puncture needle, an amplification product container element having a blade, a sealing diaphragm, a piece of glass fiber paper, and a test strip sealing part having a transparent window; and the outer casing comprises a handle cover, a fixing case pressing part, a washing buffer vacuole extruding part, and a transparent window.

PRIOR ART DOCUMENTS

Patent Documents

Patent Document 1: JP 2015-512250 A
Patent Document 2: JP 2010-500009 A

SUMMARY

Patent Documents 1, 2, and other documents disclose a device comprising a housing that accommodates a chromatography support where a part of the container accommodating the liquid is broken to leak the liquid and the liquid is brought into contact with the chromatography support.

When the liquid-accommodating container is to be broken, however, the negative pressure is created inside the container when a part of the liquid leaks from the container, and the liquid would no longer leak.

The present inventors have conducted concentrated studies and found that the liquid leaked from the container could be efficiently brought into contact with the chromatography support by perforating or incising the container together with the chromatography support in a housing accommodating the chromatography support when breaking a part of the liquid-accommodating container to leak the liquid. When the container and the chromatography support are to be perforated or incised together by means of the perforation/incision part, such as a blade, the chromatography support would be misaligned from the perforation/incision part and would not be perforated or incised thereby. In addition, when the container and the chromatography support are together pushed toward the perforation/incision part to perforate or incise the container, a great force would be used due to resistance caused by the chromatography support.

As described above, chromatography techniques involve the use of various types of liquids, such as a sample liquid containing detection targets or developing liquids. In general, such liquids are mainly composed of water. In addition, when a surface of a housing and/or a chromatography support on which the liquid leaked from the container comes into contact with the housing and/or the chromatography support has a large water contact angle, the liquid leaked from the container inside the housing forms droplets and easily migrates inside the housing, and the amount of the liquid that comes into contact with the chromatography support decreases. When the surface of a perforation/incision part, such as a blade, for perforating or incising the liquid-accommodating container of the housing has a large water contact angle, one or more embodiments arises. When a perforation/incision part with a large water contact angle on the surface forms a leakage port on the liquid-accommodating container, specifically, it is difficult to leak the liquid with low affinity with the surface of the perforation/incision part through the leakage port from the container in the presence of the perforation/incision part at the leakage port of the container.

The test device according to one or more embodiments of the present invention comprises:
a housing accommodating a chromatography support,
wherein the housing comprises:
a supporting part that supports a container accommodating a liquid used for chromatography; and a blade with an edge provided thereon that incises the container supported by the supporting part to leak a liquid from the container to a position where the liquid comes into contact with the support, and wherein the supporting part comprises a container guide that supports the container and guides the container from a first position where one end of the container faces the blade edge to a second position where the container is incised by the blade from the one end of the container, and when a length of the container supported by the supporting part in a direction guided by the container guide is designated "M," and a maximal length of an incision formed on the container in the guiding direction when the container is supported by the supporting part and guided from the first position to the second position is designated "D,"

D/M is 0.2 or greater.

Concerning the test device according to one or more embodiments of the present invention, when the container is supported by the supporting part and guided from the first position to the second position, an incision of 0.2 M or larger (=D) is formed on the container based on the length M in the container guiding direction. When a container that accommodates liquid to the depth of less than D, which is equivalent to the maximal length of the incision, on one side thereof with the remaining part in the container being composed of a gas phase is supported by the supporting part of the housing of the test device according to one or more embodiments and guided from the first position to the second position, accordingly, an incision is formed by the blade on the container to the position surrounding the gas phase inside the container. In this case, air is supplied to the gas phase from the outside of the container through the position of the incision formed on the container where the gas phase comes into contact with the outside of the container. Thus, it is less likely to create a negative gas pressure inside the container when the liquid leaks from the container and the liquid can efficiently leak from the container. To this end, a liquid can be accommodated in the container to the depth of less than D; that is, to the depth of at least less than 0.2 M.

The test device according to one or more embodiments of the present invention comprises:

a housing accommodating a chromatography support, wherein the housing comprises:

a supporting part that supports a container accommodating a liquid used for chromatography; and a blade with an edge provided thereon that incises the container supported by the supporting part to leak a liquid from the container to a position where the liquid comes into contact with the support, and wherein the supporting part comprises a container guide that supports the container and guides the container from a first position where one end of the container faces the blade edge to a second position where the container is incised by the blade from the one end of the container, and when the container is supported by the supporting part in the first position, the distance in a vertical direction from an end of the container to a liquid surface when the liquid is accommodated in the container is designated "A" and a maximal length in the vertical direction of an incision formed on the container when the container is guided from the first position to the second position is designated "B,"

B is greater than A.

When the container accommodating a liquid used for chromatography together with the gas phase is supported by the supporting part of the housing of the test device according to one or more embodiments in the first position and guided from the first position to the second position, the container is incised by the blade from the one end of the container to the position surrounding the gas phase inside the container. In this case, air is supplied to the gas phase from the outside of the container through the position of the incision formed on the container where the gas phase comes into contact with the outside of the container. Thus, it is less likely to create a negative gas pressure inside the container when the liquid leaks from the container and the liquid can efficiently leak from the container.

According to one or more embodiments of the test device, the blade is a plate-like blade comprising an edge on one side and a base end on the other end, an inner wall surface of the housing comprises a fixing part that flanks the blade in a thickness direction to fix the base end of the blade formed thereon, the fixing part comprises a tapered end that makes a dimension of the fixing part in a thickness direction of the blade to become smaller toward the blade edge, and when the container is supported by the supporting part and guided from the first position to the second position, the tapered end of the fixing part is inserted into the incision formed on the container.

According to one or more embodiments, the tapered end of the fixing part is inserted into an incision formed on the container that is supported by the supporting part and guided from the first position to the second position. Thus, a liquid can leak from the container more efficiently.

According to one or more embodiments of the present aspect, the tapered end of the fixing part has a concave-convex surface that is protruded and/or recessed in the thickness direction of the blade.

When the tapered end of the fixing part is inserted into an incision formed on the container, according to one or more embodiments, a gap is likely to be formed between the incision of the container and the concave-convex surface of the tapered end of the fixing part. Thus, a liquid is more likely to leak from the container.

One or more embodiments of the present invention provides a method for performing chromatography using a test device, wherein the test device comprises:

a chromatography support; and a housing for accommodating the support, the housing comprises:

a supporting part that supports a container accommodating a liquid used for chromatography, and a blade with an edge provided thereon that incises the container supported by the supporting part to leak a liquid from the container to a position where the liquid comes into contact with the support, the supporting part comprises a container guide that supports the container and guides the container from a first position where one end of the container faces the blade edge to a second position where the container is incised by the blade from the one end of the container, the method comprises:

step 1 of allowing the supporting part of the test device to support the container that accommodates the liquid used for chromatography together with a gas phase in the first position; and subsequent step 2 of guiding the container from the first position to the second position, and when a distance in a vertical direction from an end of the container supported by the supporting part in the step 1 to a liquid surface in the container is designated "A," and a maximal length in the vertical direction of an incision formed on the container in the step 2 is designated "B,"

B is greater than A.

According to the method of one or more embodiments, an incision is formed by the blade on the container when the container that accommodates a liquid used for chromatography is supported by the supporting part of the housing of the test device and guided from the first position to the second position. In this case, air is supplied to the gas phase from the outside of the container through the position of the incision formed on the container where the gas phase comes into contact with the outside of the container. Thus, it is less likely to create a negative gas pressure inside the container when the liquid leaks from the container and the liquid can efficiently leak from the container.

The test device according to one or more embodiments of the present invention comprises:

a chromatography support; and a housing accommodating the chromatography support, wherein the housing comprises:

a supporting part that supports a container accommodating a liquid used for chromatography, and a perforation/incision part that perforates or incises the container supported by the supporting part and the support to leak a liquid from the container to a position where the liquid comes into contact with the support, and wherein the support comprises, at a position that comes into contact with the perforation/incision part, a perforation/incision target part provided thereon in advance, which is more easily to be perforated or incised by the perforation/incision part, compared with other parts of the support.

The test device of one or more embodiments comprises, at a position that comes into contact with the perforation/incision part on the chromatography support, a perforation/incision target part provided thereon in advance. When the container and the chromatography support are perforated or incised together by the perforation/incision part, such as a blade, accordingly, the chromatography support is less likely to be misaligned from the perforation/incision part, and the container and the chromatography support can be easily perforated or incised together. When the chromatography support and the container are perforated or incised together by the perforation/incision part, in addition, resistance caused by the chromatography support is small. Compared with the use of the chromatography support without the perforation/incision target part, accordingly, the container and the chromatography support can be easily perforated or incised together with a relatively small force.

According to one or more embodiments of the test device, the support is accommodated in the housing in a manner such that the perforation/incision target part of the support is positioned between the supporting part and the perforation/incision part, and the supporting part comprises a container guide that supports the container and guides the container from a first position where the container faces the perforation/incision part through the perforation/incision target part of the support to a second position where the container and the perforation/incision target part of the support are perforated or incised together by the perforation/incision part.

In the test device of one or more embodiments, the liquid leaked from the container in the second position comes into contact with the chromatography support immediately. Thus, the liquid is absorbed more easily.

According to one or more embodiments of the test device, the perforation/incision target part is one or more elements selected from the group consisting of:

an incision that penetrates through the support in a thickness direction;

a groove formed on a part of the support in a thickness direction;

a hole that penetrates through the support in a thickness direction; and a line of perforation comprising two or more elements selected from among the incision that penetrates through the support in a thickness direction, the groove formed on a part of the support in a thickness direction, and the hole that penetrates through the support in a thickness direction.

The chromatography support comprises such perforation/incision target part provided thereon in advance, since the perforation/incision target part is perforated or incised by the perforation/incision part.

According to one or more embodiments of the test device, the length of the perforation/incision target part along the perforation/incision part is 1 mm or greater.

The chromatography support comprises the perforation/incision target part with the length of 1 mm or greater along the perforation/incision part provided thereon in advance, since the perforation/incision target part is perforated or incised by the perforation/incision part.

According to one or more embodiments of the test device, the support comprises one or more perforation/incision target parts provided thereon in advance.

The chromatography support comprises one or more perforation/incision target parts provided thereon in advance, since the part(s) is(are) perforated or incised by the perforation/incision part.

The test device according to one or more embodiments of the present invention comprises:

a chromatography support; and a housing for accommodating the support, wherein the housing comprises:

a supporting part that supports a container accommodating a liquid used for chromatography; and a perforation/incision part that perforates or incises the container supported by the supporting part to leak a liquid from the container to a position where the liquid comes into contact with the support, and wherein a surface of the housing and/or a surface of the support with which the liquid leaked from the container comes into contact has a water contact angle of 90 degrees or smaller.

In the test device of one or more embodiments, the liquid leaked from the container inside the housing sufficiently wets the surfaces of the housing and/or the support with which the liquid comes into contact. Thus, the liquid easily comes into contact with the chromatography support and it is sufficiently absorbed thereby. According to one or more embodiments in which the surface of the perforation/incision part of the housing has a water contact angle of 90 degrees or smaller, the liquid smoothly leaks from the leakage port of the container formed by perforation or incision of the perforation/incision part, and an intended amount of the liquid can be smoothly supplied to the chromatography support. Thus, testing conditions on the chromatography support are easily stabilized.

Concerning the test device described above, the surface of the housing and/or the surface of the support having a water contact angle of 90 degrees or smaller is treated by a hydrophilic treatment. In such a case, wettability of the surface of the housing and/or that of the support is further improved.

According to one or more embodiments of the test device,
the support is accommodated in the housing in a manner such that a part of the support is positioned between the supporting part and the perforation/incision part, and
the supporting part comprises a container guide that supports the container and guides the container from a first position where the container faces the perforation/incision part through the perforation/incision target part of the support to a second position where the container and the perforation/incision target part of the support are perforated or incised together by the perforation/incision part.

In the test device of one or more embodiments, the liquid leaked from the container in the second position comes into contact with the chromatography support immediately. Thus, the liquid is absorbed more easily. Even if the liquid leaked from the container is not absorbed by the chromatography support immediately, it adheres to the wall of the housing, and it remains in that site while wetting the wall. Thus, such liquid is absorbed by the chromatography support with the elapse of time. According to one or more embodiments in which the surface of the perforation/incision part of the housing has a water contact angle of 90 degrees or smaller, the liquid smoothly leaks from the container broken by the perforation/incision part, and an intended amount of the liquid can be smoothly supplied to the chromatography support.

This description includes part or all of the contents as disclosed in the descriptions and/or drawings of Japanese Patent Application Nos. 2017-215975, 2017-215984, and 2017-215977, which are priority documents of the present application.

With the use of the test device and the method according to one or more embodiments of the present invention, the liquid used for chromatography can be efficiently leaked from the container.

In the test device according to one or more embodiments of the present invention, a perforation/incision target part is provided on the chromatography support in a part that comes into contact with the perforation/incision part. When the container and the chromatography support are perforated or incised together by the perforation/incision part, accordingly, the chromatography support is less likely to be misaligned from the perforation/incision part, and the container and the chromatography support can be perforated or incised together. When the chromatography support and the container are perforated or incised together by the perforation/incision part, in addition, resistance caused by the chromatography support is small. Accordingly, the container and the chromatography support can be easily perforated or incised together with a small force.

In the test device according to one or more embodiments of the present invention, the liquid leaked from the container inside the housing sufficiently wets the surfaces of the housing and/or the support with which the liquid comes into contact. Thus, the liquid easily comes into contact with the chromatography support and it is sufficiently absorbed thereby. Thus, testing conditions on the chromatography support are easily stabilized.

BRIEF DESCRIPTION OF THE DRAWINGS

FIGS. 9A-9B shows a structure of a chromatography support that can be used in one or more embodiments of the present invention. 9A shows a plane view, and 9B shows a lateral view.

DETAILED DESCRIPTION

Figure 1A:
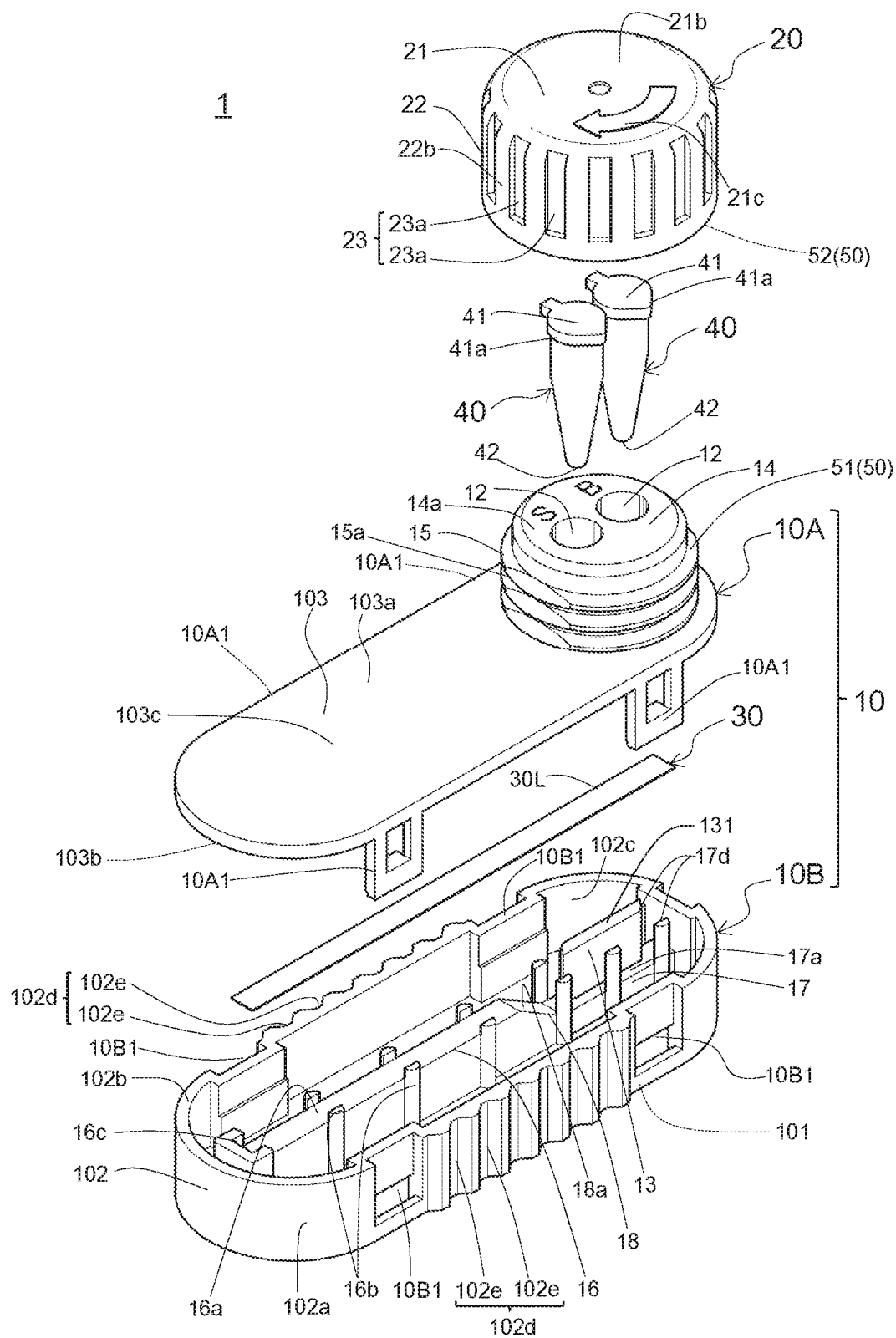
FIG. 1A shows an exploded perspective view of the test device according to one or more embodiments of the present invention.

Hereafter, one or more embodiments of the present invention are described with reference to the drawings, although the scope of one or more embodiments of the present invention is not limited to one or more embodiments shown in the drawings.

Summary of the Test Device

Figure 1B:
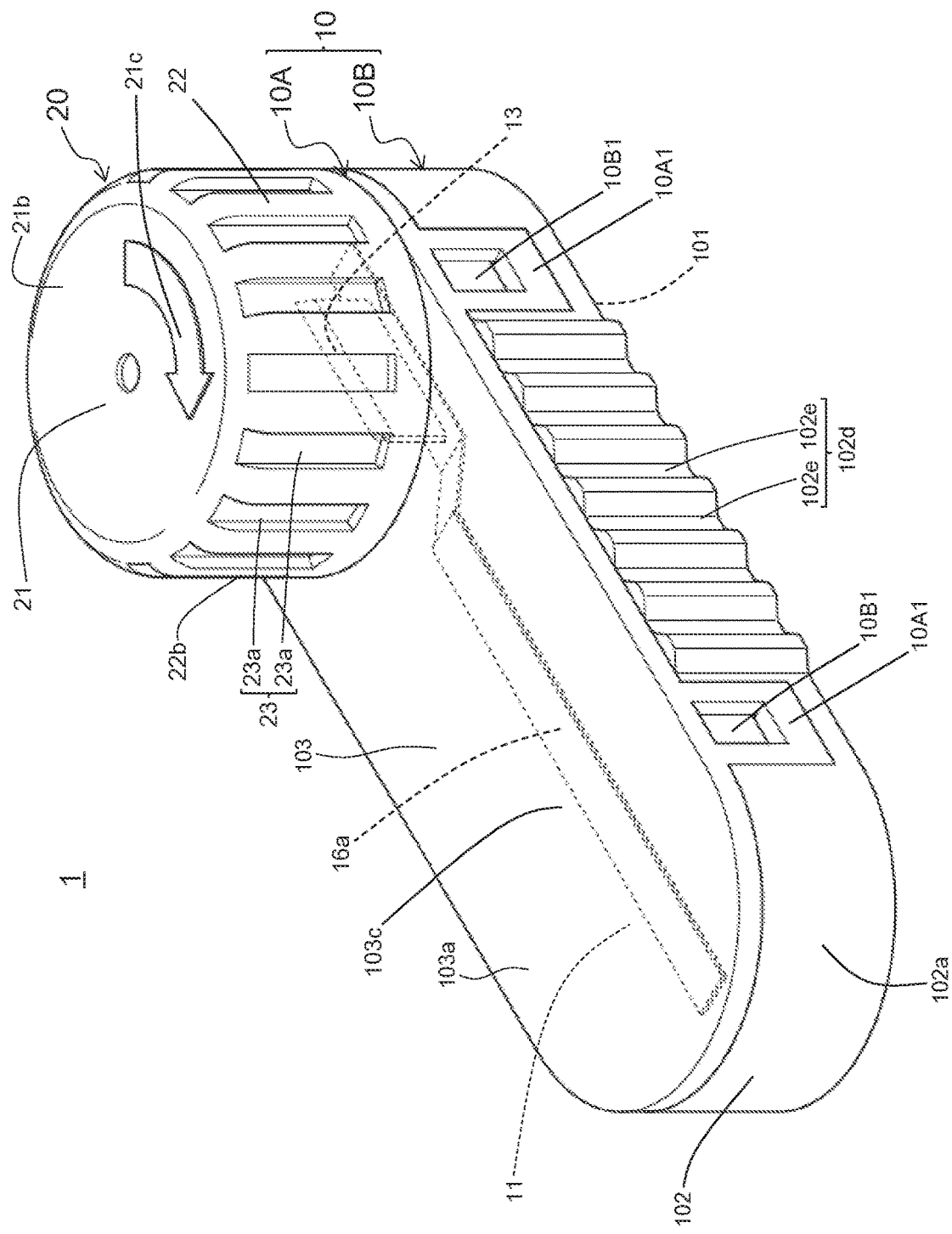
FIG. 1B shows a perspective view of the test device according to one or more embodiments of the present invention.
Figure 1C:
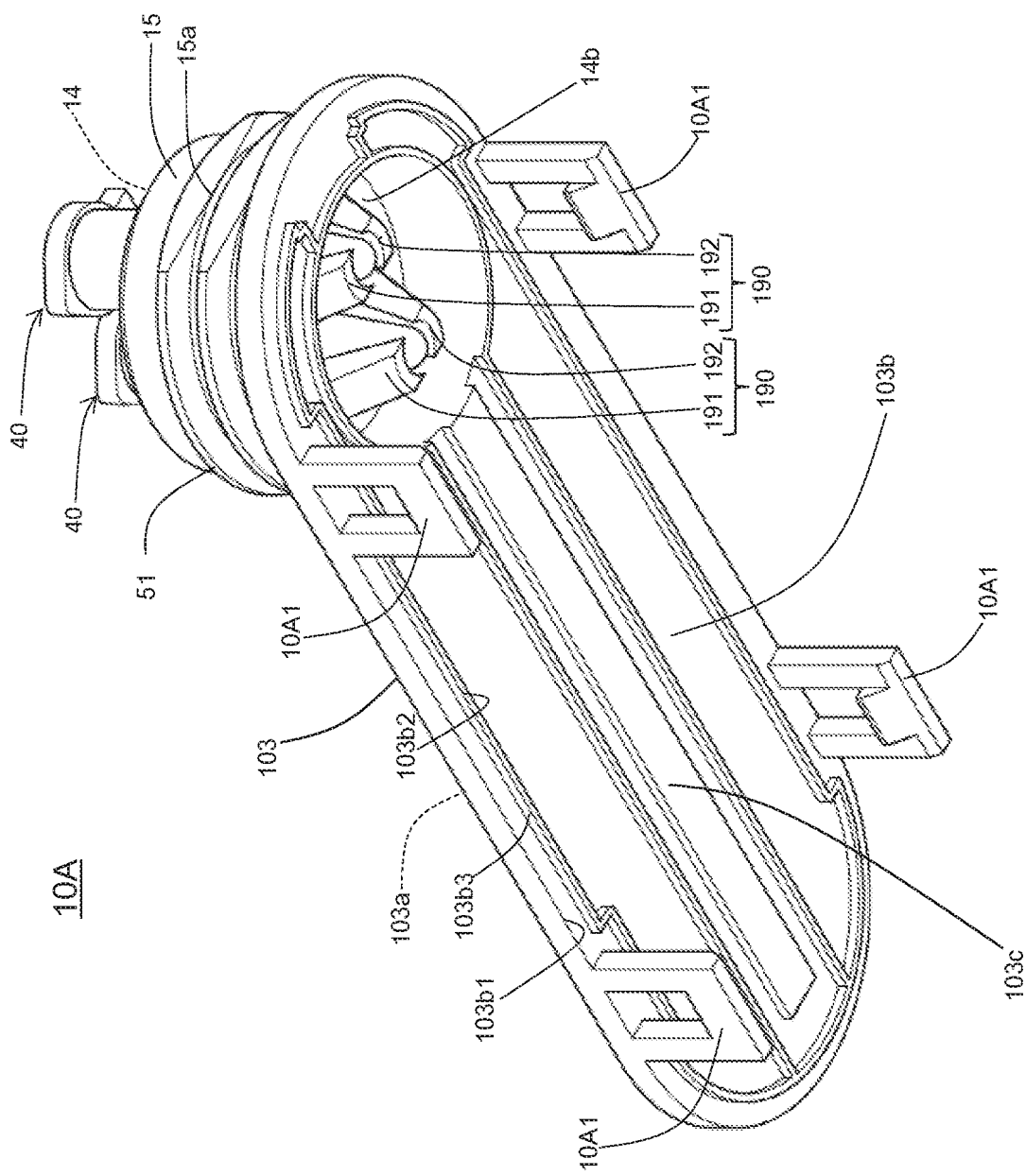
FIG. 1C shows a perspective view taken from the underneath of an upper housing member of the test device according to one or more embodiments of the present invention.
Figure 2:
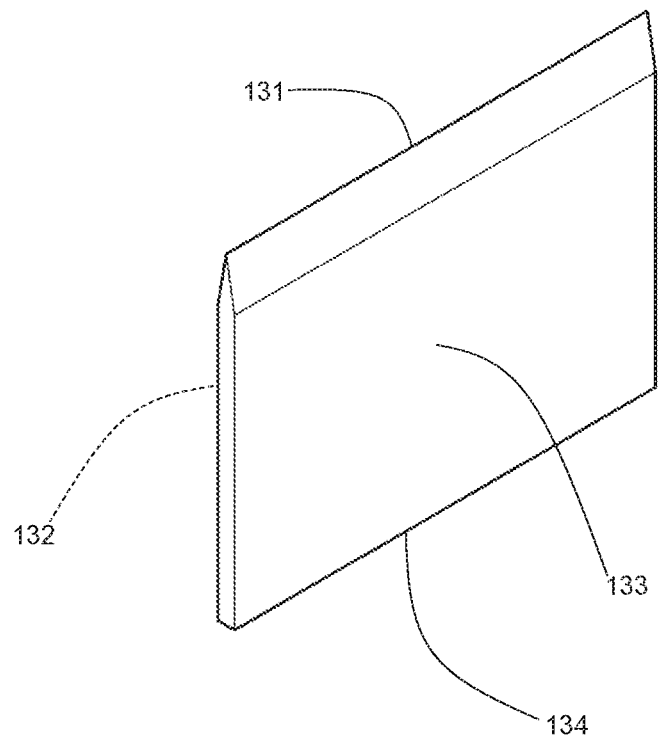
FIG. 2 shows a perspective view of a blade (a perforation/incision part) of the test device according to one or more embodiments of the present invention.

The test device 1 according to one or more embodiments of present invention is described with reference to FIG. 1A to FIG. 2.

The test device 1 according to the one or more embodiments comprises a housing 10 and a lid 20. Materials constituting the housing 10 and the lid 20 are not particularly limited, and materials, such as resin and glass, can be adequately used. As described below, the test device of one or more embodiments of the present invention does not necessarily comprise the lid 20 of the test device 1 according to one or more embodiments.

The housing 10 encloses an internal space 11 that accommodates a chromatography support 30.

The housing 10 also comprises a perforation/incision part (blade) 13 where containers 40 provided inside the internal space 11 are perforated or incised to allow liquids L to leak from the containers 40 to the position where liquids come into contact with the chromatography support 30.

According to one or more embodiments shown in the figure, the housing 10 is composed of an upper housing member 10A and a lower housing member 10B. The lower housing member 10B comprises a bottom wall 101 of the housing 10 and a side wall 102 rising upright from the periphery of the bottom wall 101. The upper housing member 10A comprises an upper wall 103 of the housing 10, the supporting part 14 of the housing described below, and a lid-mounting part 15. In the upper wall 103 of the upper housing member 10A, a surface serving as an outer surface of the housing 10 in combination with the lower housing member 10B is designated as an upper surface 103a, and a surface serving as an inner surface of the housing 10 in combination with the lower housing member 10B is designated as a lower surface 103b. In the periphery of the upper wall 103 of the upper housing member 10A, four latching convex parts 10A1 protruding toward the lower surface 103b are formed, and four latching concave parts 10B1 engaged with the latching convex parts 10A1 are formed on an outer surface 102 of the side wall 102 of the lower housing member 10B.

The upper edge 102b of the side wall 102 of the lower housing member 10B abuts against the peripheral area 103b1 of the lower surface 103b of the upper wall 103 of the upper housing member 10A when the upper housing member 10A is engaged with the lower housing member 10B. In addition, a protrusive part 103b2 is provided on the lower surface 103b of the upper wall 103 in such a manner that it is adjacent to the inner periphery along the peripheral area 103b1 and protrudes from the peripheral area 103b1. When the upper housing member 10A is engaged with the lower housing member 10B, the outer peripheral surface 103b3 of the protrusive part 103b2 on the lower surface 103b of the upper wall 103 of the upper housing member 10A abuts against an area adjacent to the upper edge 102b of the inner surface 102c of the side wall 102 of the lower housing member 10B. When the upper housing member 10A is engaged with the lower housing member 10B to form the housing 10, a liquid can be prevented from leaking from the boundary between the side wall 102 and the upper wall 103.

According to one or more embodiments shown in the figure, the housing 10 is composed of two members (i.e., the upper housing member 10A and the lower housing member 10B). Members constituting the housing 10 are not limited thereto, and the housing 10 may be composed of a single member or three or more members.

The internal space 11 is enclosed in the housing 10. According to one or more embodiments shown in the figure, the internal space 11 is communicated with the external air through the holes 12 while other areas are closed. According to one or more embodiments shown in the figure, a main unit of the housing 10 is composed of the bottom wall 101, the side wall 102, and the upper wall 103 surrounding the internal space 11.

The inner wall surface of the housing is exposed to the internal space. According to one or more embodiments shown in the figure, the inner wall surface of the housing is a surface of a member, such as the bottom wall 101, the side wall 102, or the upper wall 103, defining the internal space 11 of the housing 10. The inner wall surface is exposed to the internal space.

The supporting part 14 is provided with one or more holes 12 as container guides that support one or more containers 40 (two containers according to one or more embodiments shown in the figure) accommodating liquids L used for chromatography and guiding the containers 40 from the first position to the second position. The holes 12 function as guiding holes that guide the containers 40 inserted into the holes 12 and supported thereby from the first position to the second position described below with respect to one or more embodiments of the present invention. A container guide is not limited to the hole 12 formed on the supporting part 14, provided that it is capable of guiding the container from the first position to the second position described below. The holes 12 are through holes that allow communication between the internal space 11 and the outside of the housing 10. The configuration of the holes 12 is not particularly limited, provided that the containers 40 can be inserted into the holes 12 and supported thereby in a through-hole direction, and the containers 40 can be guided to migrate toward the perforation/incision part 13. The symbol "S" indicated on the outer surface 14a of the supporting part 14 shown in FIG. 1A is a label indicating a hole 12 that comprises containers 40 accommodating the sample solution as a liquid L, and "B" is a label indicating that the hole 12 comprises the containers 40 accommodating developing solutions (buffers) as liquids L.

In the internal space 11 of the housing 10, chromatography is carried out. A solid-phase chromatography support 30 is provided in the internal space 11. In the internal space 11, chromatography is carried out when liquid L comes into contact with a part of the chromatography support 30 and develops in the chromatography support 30.

Examples of liquid L include a sample liquid containing detection targets in a medium such as water, a developing liquid, and a liquid containing labeling agents in a medium such as water. The medium is typically water. Examples of sample liquids include sample liquids containing amplified products of nucleic acids. Examples of developing liquids include phosphate buffer, Tris buffer, Good's buffer, and SSC buffer. A developing liquid may further contain a surfactant. A liquid L may be a mixture containing one or more of a sample liquid, a developing liquid, and a liquid containing a labeling agent. Alternatively, a liquid containing a color reagent or a dye may be used as liquid L. In the drawings and descriptions provided below, liquids accommodated in a plurality of containers 40 and a liquid released into the internal space 11 are collectively referred to as "liquid L," and each liquid L accommodated in one of a plurality of containers 40 may be of different compositions. Containers 40 that accommodate liquids L other than the sample liquid may be inserted into the holes 12 in advance.

The chromatography support 30 provided in the internal space 11 of the housing 10 is not limited, provided that it is a solid-phase support. A support composed of a resin, metal, polysaccharide, mineral, or other material may be used in the form of, for example, a membrane, film, unwoven fabric, plate, or gel. According to one or more embodiments shown in the figure, a configuration of the chromatography support 30 is a thin and long membrane (a strip), although the configuration is not limited thereto. The chromatography support 30 has a porous structure. Specific examples of the chromatography support 30 include paper, a nitrocellulose membrane, a polyether sulfone membrane, a nylon membrane, various types of dehydrated gels (e.g., silica gel, agarose gel, dextran gel, and gelatin gel), silicon, glass, and resin.

In a part of the chromatography support 30, a capture substance for capturing detection targets can be provided. When detection targets contain nucleic acids, for example, nucleic acids hybridizing to such nucleic acids can be used as capture substances. When detection targets contain antigens or antibodies, antigens or antibodies immunologically reacting with such antigens or antibodies can be used as capture substances.

Detection targets can be visually detectable on the chromatography support 30. For example, detection targets may be labeled with labeling agents enabling visual detection of the detection targets and developed on the chromatography support 30. Thus, the detection targets can be visually detected. Examples of labeling agents enabling visual detection include colored particles, dyes, and fluorescent substances. Examples of "colored particles" include metal (e.g., gold, silver, copper, and platinum) particles, latex particles containing metal nanorods, metal nanoplates, dyes, and fluorescent substances, and silica nanoparticles including dyes and fluorescent substances. A method for labeling detection targets with labeling agents enabling visual detection is not particularly limited. When detection targets contain nucleic acids, for example, labeling agents to which nucleic acids hybridizing to the nucleic acids of interest are ligated may be brought into contact with the detection targets. Thus, detection targets can be labeled with labeling agents. From the viewpoint of visual detection, at least a part of a wall surrounding the internal space 11 of the housing 10 is formed of a material through which a visible light can penetrate, so that the chromatography support 30 can be observed from the outside of the housing 10. In particular, a part 103c positioned to face the part of the upper wall 103 of the housing 10 where the chromatography support 30 is to be positioned is formed of a material through which a visible light can penetrate.

FIGS. 9A-9B and FIGS. 14A-14B each show the structure of the chromatography support 30 used in the one or more embodiments. In one or more embodiments, the chromatography support 30 comprises a liquid receiver 31 and a detection part 32. The liquid receiver 31 is positioned at one end of the detection part 32 and liquid L is supplied thereto. In the detection part 32, detection targets are developed. An absorption pad 33 is positioned at another end of the detection part 32. A labeling agent holder 34 for holding the labeling agents is positioned in a space between the liquid receiver 31 and the detection part 32. When liquid L supplied to the liquid receiver 31 contains detection targets, the detection targets are first labeled with labeling agents when passing through the labeling agent holder 34, and the detection targets then migrate to the detection part 32. When detection targets are labeled in advance or liquid L contains labeling agents, a labeling agent holder 34 can be foregone, the liquid receiver 31 can be located in a position adjacent to the detection part 32, or the liquid receiver 31 can be omitted. The detection part 32 comprises a capture region 321 on which the capture substance for capturing detection targets is provided. The liquid receiver 31, the labeling agent holder 34, the detection part 32, and the absorption pad 33 can be composed of the materials described above, so that these components can be used for the chromatography support 30. These components may be composed of the same or different members. The liquid receiver 31, the labeling agent holder 34, the detection part 32, and the absorption pad 33 can be positioned on a substrate 35, as shown in the figures. The substrate 35 can be composed of a resin, metal, polysaccharide, mineral, or other material. The substrate 35 can be partially or completely omitted. For example, a substrate equivalent to the lower portion of the liquid receiver 31 may be partially or completely omitted. Thus, flexibility of the liquid receiver 31 can be improved, and resistance caused when the containers 40 is pushed toward the perforation/incision part can be reduced. Similar effects can also be attained with the use of a highly flexible substrate. A constitution of the chromatography support 30 is not limited to the constitution shown in FIGS. 9A-9B, and a chromatography support with an adequate constitution can be selected in accordance with chromatography of interest.

Another example of the chromatography support 30 consists of the detection part 32 that does not comprise the liquid receiver 31, the labeling agent holder 34, the absorption pad 33, and the substrate 35, as shown in FIGS. 10A-10B and FIGS. 15A-15B. The chromatography support 30 that consists of the detection part 32 and the substrate 35 supporting the detection part 32 can also be used (not shown).

In the internal space 11 of the housing 10 according to one or more embodiments, when the chromatography support 30 comprises the labeling agent holder 34, the liquid receiver 31 comes into contact with liquid L leaked from the containers 40, but the detection part 32 and the absorption pad 33 are positioned to avoid direct contact with the leaked liquid L. As described above, the labeling agent holder 34 can be omitted from the chromatography support 30 when, for example, liquid L contains labeling agents. Also, the chromatography support 30 consisting of the detection part 32 or the chromatography support 30 consisting of the detection part 32 and the substrate 35 can be used as described above. When the chromatography support 30 from which the labeling agent holder 34 is omitted, the chromatography support 30 consisting of the detection part 32 as shown in FIGS. 10A-10B and FIGS. 15A-B, or the chromatography support 30 consisting of the detection part 32 and the substrate 35 are used, and liquid L leaked from the containers 40 may be positioned to be in direct contact with the detection part 32.

Hereafter, a region of the chromatography support 30 that comes into direct contact with liquid L leaked from the containers 40 is referred to as a "liquid contact part 30L."

The internal space 11 of the housing 10 is provided with a support-mounting part 16 where the chromatography support 30 rising upright from the bottom wall 101 toward the internal space 11 is provided. The support-mounting part 16 is constituted in such a manner that the chromatography support 30 is positioned to face the part 103c of the upper wall 103 in a position closer to the upper wall 103 between the bottom wall 101 and the upper wall 103 in the direction in which the bottom wall 101 and the upper wall 103 of the housing face each other. The detection part 32 and the absorption pad 33 of the chromatography support 30 are provided on an upper surface 16a of the support-mounting part 16. In contrast, the liquid contact part 30L is positioned between the supporting part 14 and the perforation/incision part 13 of the housing 10. The detection part 32 and the absorption pad 33 of the chromatography support 30 may be fixed to the upper surface 16a of the support-mounting part 16 with the aid of an adhesive agent or a pressure-sensitive adhesion tape. Liquid L leaked from the containers 40 perforated or incised at the perforation/incision part 13 would not reach the upper surface 16a of the support-mounting part 16. When the housing 10 is disposed on a horizontal surface, specifically, the upper surface 16a is located in a position higher than the position where liquid L leaks from the container into the internal space 11. The upper surface 16a of the support-mounting part 16 has a planar configuration in accordance with a region comprising the detection part 32 and the absorption pad 33 of the chromatography support 30. According to one or more embodiments shown in the figure, the upper surface 16a has a configuration with a longitudinal direction and a short-width direction. The support-mounting part 16 comprises a plurality of positioning protrusive parts in positions surrounding the upper surface 16a. The positioning protrusive parts regulate migration of the chromatography support 30 toward the upper surface 16a and execute positioning of the chromatography support 30. Positioning protrusive parts are composed of the first positioning protrusive parts 16b positioned at both sides of the short-width direction of the upper surface 16a and the second positioning protrusive parts 16c positioned at one end of the upper surface 16a in the longitudinal direction.

According to one or more embodiments shown in the figure, the number of holes 12, which are container guides formed on the supporting part 14 of the housing 10 is 2. The number thereof may be 1, it may be 3 or greater, and it may be determined in accordance with the number of containers 40 accommodating liquids L used for chromatography of interest. When a sample liquid and a developing liquid are used as liquids L, for example, two holes 12 are formed. In such a case, two holes 12 can be formed in positions facing the position where the chromatography support 30 is provided in the internal space 11 in the direction of chromatographic development, the containers 40 accommodating a sample liquid be inserted into the hole 12 located downstream in the direction of chromatographic development, and the containers 40 accommodating a developing liquid be inserted into the hole 12 located upstream in the direction of chromatographic development. Thus, the amount of detection targets reaching the detection part 32 is increased, although the positions are not limited thereto. When there are two or more containers 40, configurations, color tones, and patterns of containers 40 may be different from each other, so that containers can be easily distinguished from each other. Each liquid L accommodated in each containers 40 may be colored to have a color tone different from that of liquid L to be contained in another container. When two or more containers 40 having different configurations are used, holes 12 may have different configurations to fit the configurations of relevant containers.

The lid 20 is mounted on the housing 10 to cover the supporting part 14 of the housing 10. When a liquid is present between the supporting part 14 and the lid 20, the lid 20 covers the supporting part 14 of the housing, so as to prevent the liquid from leaking to the outside of the test device 1 under normal conditions.

According to one or more embodiments, the lid 20 is composed of the main lid part 21 and the peripheral wall part 22 extending from the outer periphery of the main lid part 21 extending on the side of the inner surface 21a of the main lid part 21.

At least either one of the housing 10 and the lid 20 comprises a lid guide 50 that guides the lid 20 to the housing 10.

According to one or more embodiments, the supporting part 14 of the housing 10 is provided in a position protruded outwardly from the upper wall 103, and the supporting part 14 of the housing is connected to the upper wall 103 by the lid-mounting part 15 surrounding supporting part 14 on which the lid 20 is to be mounted.

According to one or more embodiments, the lid guide 50 is composed of a housing-side screw-engagement part 51 provided on the outer peripheral surface 15a in the lid-mounting part 15 of the housing 10 and a lid-side screw-engagement part 52 provided on the inner peripheral surface 22a in the peripheral wall part 22 of the lid 20 that can engage with the housing-side screw-engagement part 51. When the lid 20 mounted on the housing 10 is allowed to revolve with the aid of the housing-side screw-engagement part 51 and the lid-side screw-engagement part 52, the lid 20 is guided by the lid guide 50 and allowed to migrate toward the supporting part 14 of the housing 10 in the direction X.

In order to allow the lid 20 to revolve more, as shown in the figure, provided is an anti-slip area 23 comprising a plurality of concave grooves 23a with gaps there between that extend in the direction X be provided on the outer surface 22b of the peripheral wall part 22 of the lid 20. On the outer surface 21b of the main lid part 21 of the lid 20, a label 21c that enables visual observation of the revolving direction can be provided.

The lid guide 50 is not limited to the screw-engagement part shown in the figure, and one or more embodiments may be employed. According to one or more embodiments of the lid guide 50, for example, screw-engagement parts are not provided on the outer peripheral surface 15a of the lid-mounting part 15 of the housing 10 and on the inner peripheral surface 22a of the peripheral wall part 22 of the lid 20. While the outer peripheral surface 15a of the lid-mounting part 15 of the housing 10 abuts against the inner peripheral surface 22a of the peripheral wall part 22 of the lid 20, the lid 20 is guided to the housing 10 by sliding. According to one or more embodiments, screw-engagement parts are not provided on the outer peripheral surface 15a of the lid-mounting part 15 of the housing 10 and on the inner peripheral surface 22a of the peripheral wall part 22 of the lid 20. While the outer peripheral surface 15a of the lid-mounting part 15 of the housing 10 abuts against the inner peripheral surface 22a of the peripheral wall part 22 of the lid 20 through one or more sealing parts disposed there between, the lid 20 is guided to the housing 10. A sealing part can be made of a material capable of elastic deformation, such as rubber. A sealing part may be fixed to either one of the outer peripheral surface 15a of the lid-mounting part 15 of the housing 10 and the inner peripheral surface 22a of the peripheral wall part 22 of the lid 20.

The perforation/incision part 13 perforates or incises the containers 40 supported by the supporting parts 14 and the chromatography support 30 to leak liquids L from the containers 40 to the positions where the liquids come into contact with the liquid contact part 30L of the chromatography support 30. In one or more embodiments, a blade that incises the containers 40 as shown in FIG. 2 is used as the perforation/incision part 13 (indicated as the "blade 13" when the perforation/incision part 13 is specified as the blade). The blade 13 shown in FIG. 2 is of a plate-like structure, such that the blade edge 131 is formed on one side, and the base end 134 is formed on the other side. The blade 13 shown in FIG. 2 is of a double-edge structure, such that both the lateral surface 132 and the lateral surface 133 incline in the vicinity of the edge 131 and intersect with each other at the edge 131, although the blade is not limited thereto. Alternatively, the blade 13 may be of a single-edge structure, such that either the lateral surface 132 or the lateral surface 133 inclines, the other remains flat, and the lateral surfaces intersect each other at the edge 131. According to one or more embodiments shown in the figure, the blade 13 is a rectangular plate-like blade, and a blade of other configurations, such as a parallelogram, trapezium, triangle, circle, or other shapes can be used. The perforation/incision part 13 is not limited to the blade. An example of the perforation/incision part 13 other than the blade is a needle that perforates the container 40 together with the chromatography support 30. According to one or more embodiments, a plurality of containers 40 are incised together with the chromatography support 30 at a single perforation/ incision part 13, although the constitution is not limited thereto. A plurality of perforation/incision parts 13 may be provided in accordance with the relevant containers. Materials constituting the perforation/incision part 13 are not particularly limited, provided that such materials can provide sufficient strength to perforate or incise the container 40 together with the chromatography support 30. Examples thereof include metals, such as steel, stainless steel, and aluminum, ceramics, and resin.

The perforation/incision part 13 is fixed on the inner wall surface of the housing 10, so that it is provided inside the internal space 11 of the housing 10. According to one or more embodiments, the perforation/incision part 13 is fixed on the inner wall surface 101a of the bottom wall 101 facing the holes 12 inside the internal space 11 of the housing 10, although the perforation/incision part 13 is not limited thereto. On the inner wall surface 101a of the bottom wall 101, a fixing part 17 that fixes the perforation/incision part 13 is provided. According to one or more embodiments, the fixing part 17 is provided to fix the base end 134 of the blade 13, which is the perforation/incision part, by flanking the blade 13 in the thickness direction and allow the edge 131 of the blade 13 to face the supporting part 14 inside the internal space 11. According to one or more embodiments, the fixing part 17 is arranged on the same line with the support-mounting part 16 on the bottom wall 101. When the test device 1 according to one or more embodiments is placed on a horizontal surface, the upper surface 17a of the fixing part 17 is located in a position lower than the upper surface 16a of the support-mounting part 16. The support-mounting part 16 is connected to the fixing part 17 with the connector 18 provided upright from the bottom wall 101 in the internal space 11. The upper surface 16a of the support-mounting part 16 is connected to the upper surface 17a of the fixing part 17 through the upper surface 18a of the connector 18 inclined from the upper surface 16a of the support-mounting part 16 toward the upper surface 17a of the fixing part 17. On both sides of the fixing part 17 that fixes the perforation/incision part 13 in the short-width direction of the upper surface 17a, third positioning protrusive parts 17b are provided. In accordance with the migration of the containers 40 from the first position to the second position, the perforation/incision part 13 fixed by the fixing part 17 and the liquid contact part 30L of the chromatography support 30 provided between the holes 12 migrate toward the fixing part 17. In such a case, migration of the liquid contact part 30L is restricted to the direction in which the containers 40 are guided.

As the container 40, a container that can accommodate liquid L used for chromatography, that can be inserted into the hole 12 of the housing 10 and supported thereby, and that can be perforated or incised by the perforation/incision part 13 can be used. The container 40 is typically a resin container. As the container 40, a tubular container that extends in one direction with one end being closed and the other end being open is one or more embodiments. As shown in the figure, specifically, a container that has an opening/closing part 41a at the outer end 41 outside of the housing 10 and that is closed at the inner end 42 inside of the housing 10 when the container is supported by the supporting part 14 can be used. The container 40 comprising an opening/closing part 41a at the outer end 41 as shown in the figure generally comprises, in the periphery of the opening/closing part 41a, a hinge 401 and a pinch 402 that would protrude outwardly from the profile 400 in a plane view of the outer end 41. An example of such container 40 is a microtube used for nucleic acid amplification or biochemical testing.

The supporting part 14 comprises, at a position surrounding a relevant hole 12, an elastic member 190 that urges the container 40, which is inserted into the hole 12 and supported thereby, against the axis along the through-hole direction of the hole 12 and retains the position of the container 40 in the hole 12. Specifically, the elastic member 190 is composed of a pair of elastic supporting pieces 191 and 192 protruded from a pair of positions facing each other in the vicinity of the hole 12 on the inner surface 14b facing the internal space 11 of the supporting part 14 toward the internal space 11. The pair of elastic supporting pieces 191 and 192 are positioned in a manner such that a surface 191a of an elastic supporting piece 191 faces a surface 192a of the other elastic supporting piece 192. The surface 191a of an elastic supporting piece 191 and the surface 192a of the other elastic supporting piece 192 are formed in a manner such that the distance there between becomes smaller as the distance in the direction X from the inner surface 14b of the supporting part 14 becomes larger. The pair of elastic supporting pieces 191 and 192 flank the container 40 inserted into the hole 12 and urge the container against the axis along the through-hole direction of the hole 12 to retain the position. The pair of elastic supporting pieces 191 and 192 are capable of elastic deformation. As the container 40 is pushed toward the perforation/incision part 13, the elastic supporting pieces are pushed to open in accordance with the configuration of the container 40. As shown in the figure, accordingly, the position of the container 40 can be stably maintained even with the use of the container 40 that is configured to have an increasing width from the inner end 42 toward the outer end 41. As long as the elastic supporting pieces 191 and 192 are capable of elastic deformation, a container 40 with a different width can be supported stably. According to one or more embodiments, the positions of the containers 40 inserted into the holes 12 can be maintained with the aid of the elastic member 190 composed of the pair of elastic supporting pieces 191 and 192. Thus, the position of the container 40 with respect to the perforation/incision part 13 can be stabilized, and the amount of liquid L leaking from the container 40 can be stabilized.

The test device 1 according to one or more embodiments also comprises undulated surfaces 102d formed on at least a part of the outer surface 102a of the side wall 102, which is the lateral surface of the housing 10. The undulated surfaces 102d are formed of a plurality of continuous grooves 102e in the direction in which the bottom wall 101 and the upper wall 103 of the housing 10 face each other. The undulated surfaces 102d are provided on the outer surfaces 102a of the side wall 102. This can prevent slipping that occurs when a user operates the test device with fingers. When a plurality of test devices 1 according to one or more embodiments are arranged in a manner such that the outer surfaces 102a of the side walls 102 of the housings 10 are in contact with each other, the undulated surfaces 102d can be engaged with each other. An undulated surface is an example of a concave-convex surface. In the test device 1 according to one or more embodiments, concave-convex surfaces with different configurations may be provided instead of the undulated surfaces 102d. A concave-convex surface is formed of a plurality of continuous grooves extending in one direction, and a flat surface may be formed between grooves adjacent to each other. Concerning the plurality of grooves on the concave-convex surface, a configuration of a cross section of a plane vertical to the extending direction is not particularly limited. While an example of a surface having a cross section with a curved configuration is an undulated surface shown in the figure, a configuration of the cross section may be a rectangle or U-shape.

Subsequently, features according to one or more embodiments of the present invention are described. One or more embodiments of the present invention involves the use of a blade as a perforation/incision part.

With reference to FIG. 3A to FIG. 4C, the mechanism of the test device 1 according to one or more embodiments of the present invention, such that the containers 40 inserted into the holes 12 of the supporting part 14 and supported thereby are incised by the blade 13, is described.

Figure 3A:
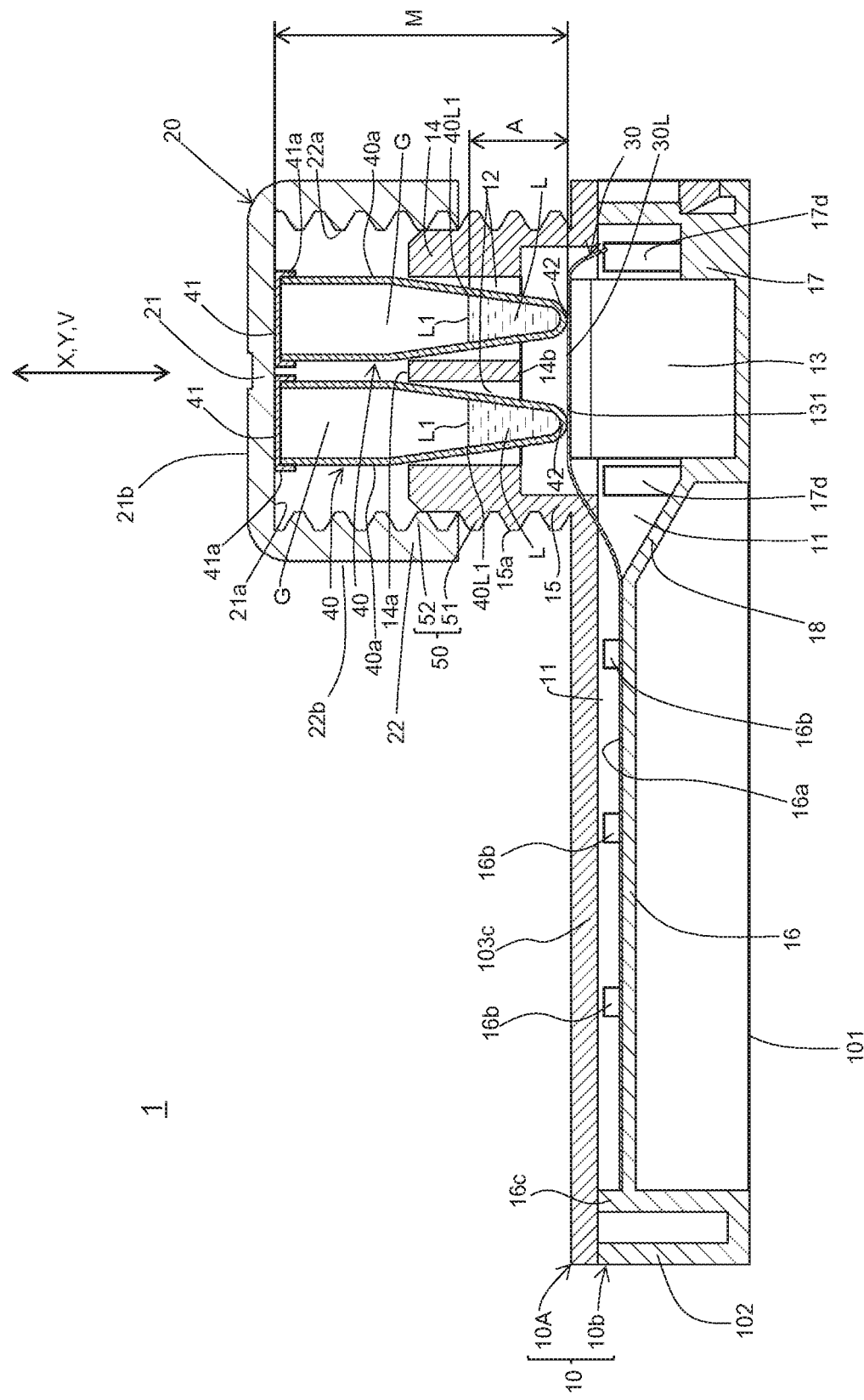
FIG. 3A schematically shows a cross section of the test device according to one or more embodiments of the present invention in a longitudinal direction in which the container is supported by the supporting part and positioned in the first position of the housing.
Figure 4A:
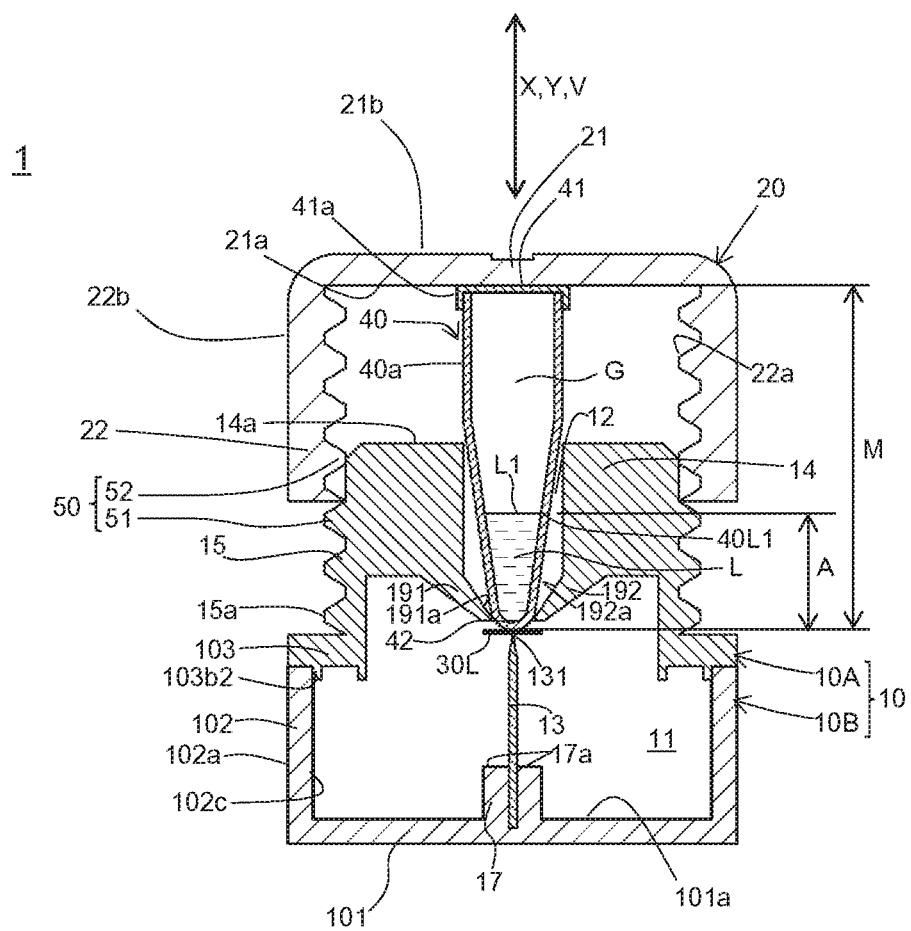
FIG. 4A schematically shows an end plane of the test device according to one or more embodiments of the present invention including a container in a short-width direction in which the container is supported by the supporting part and positioned in the first position of the housing.

FIG. 3A and FIG. 4A each show the condition in which the containers 40 each accommodating liquid L are inserted into the holes 12 of the supporting part 14 and supported thereby. In this case, the inner end 42 of the container 40 faces the edge 131 of the blade 13. The position where the container is supported by the supporting part with one end of the container facing the blade edge is defined as "the first position."

Figure 3B:
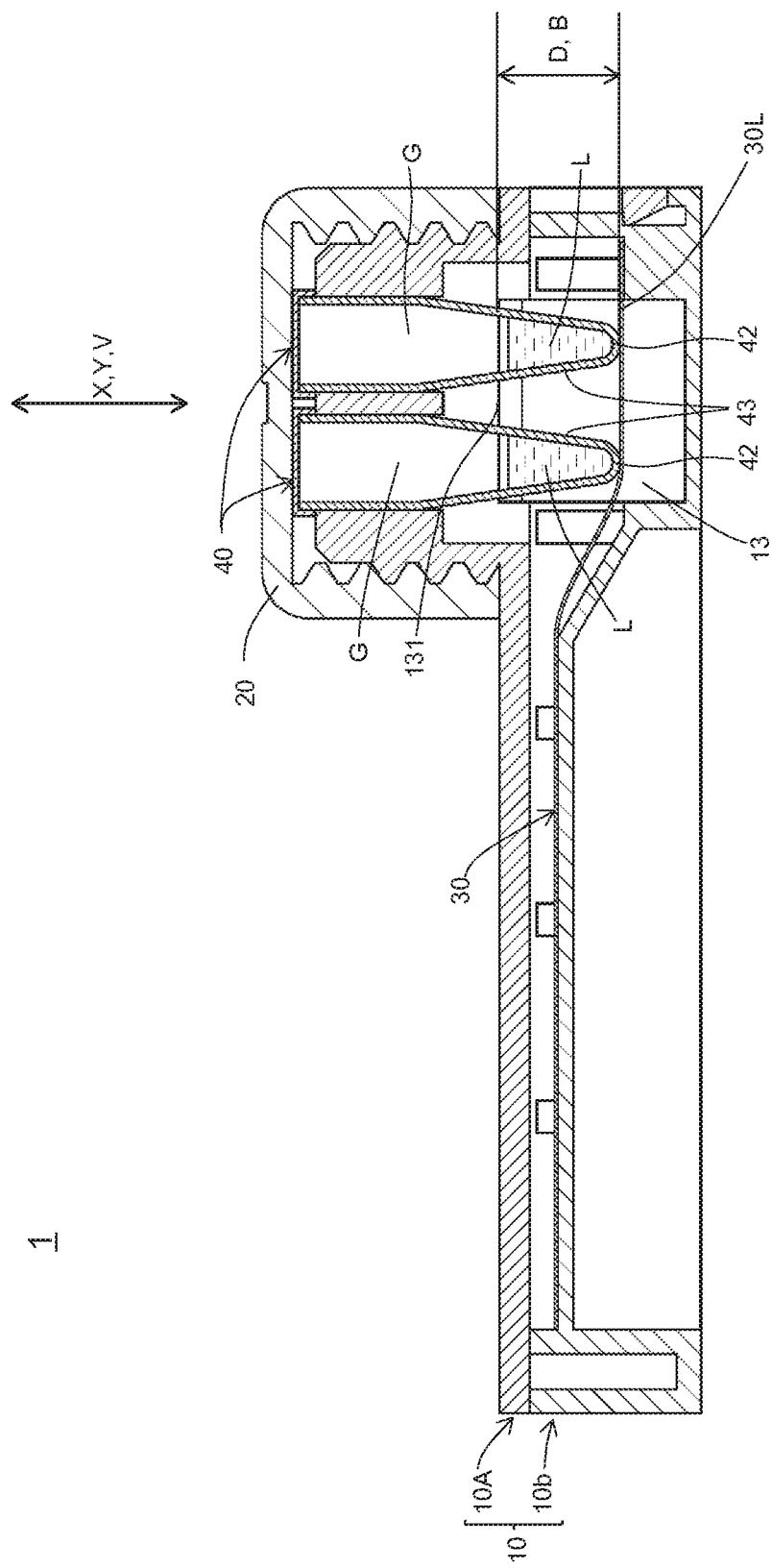
FIG. 3B schematically shows a cross section of the test device according to one or more embodiments of the present invention in a longitudinal direction in which the container is supported by the supporting part and positioned in the second position of the housing before the liquid leaks from the container.
Figure 3C:
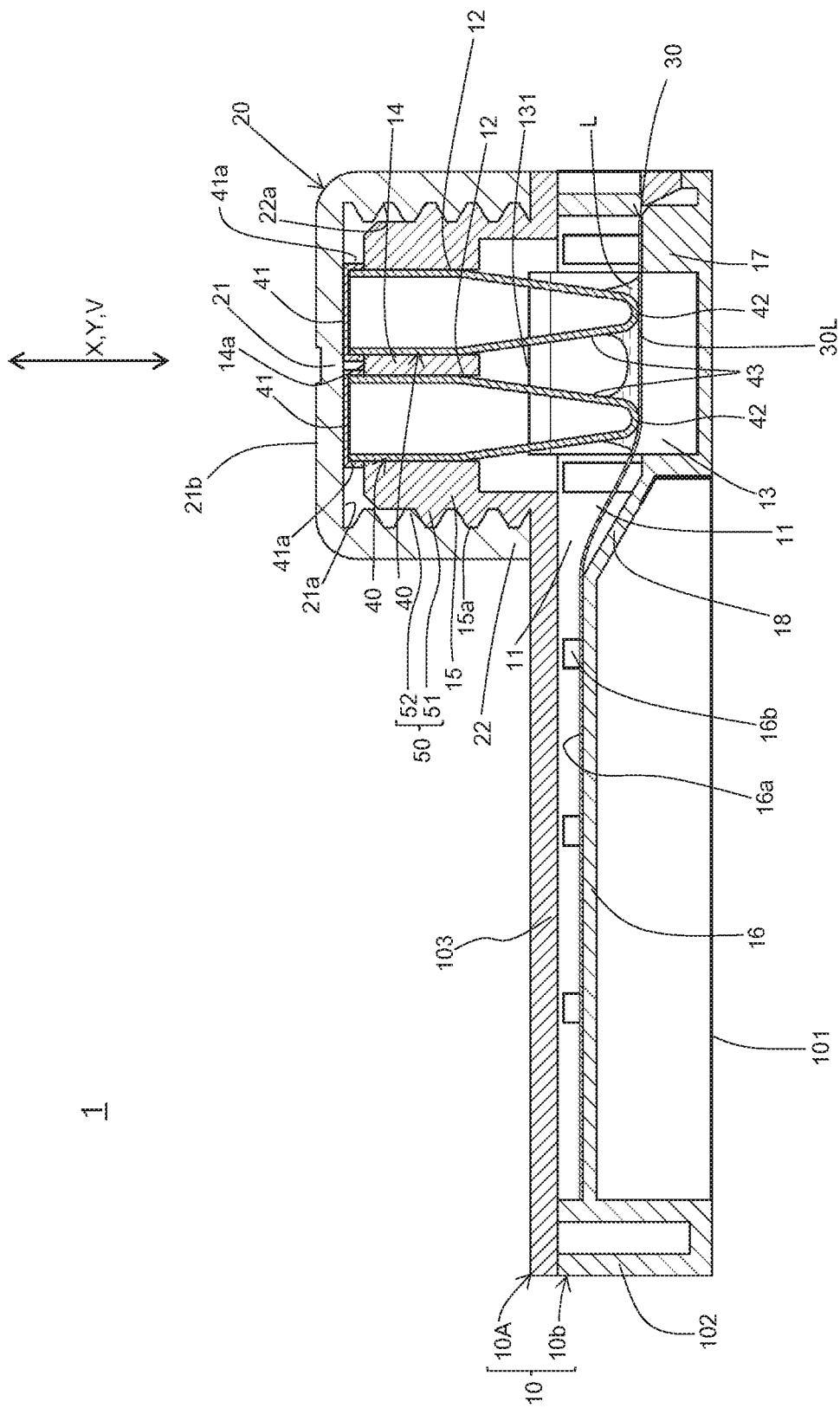
FIG. 3C schematically shows a cross section of the test device according to one or more embodiments of the present invention in a longitudinal direction in which the container is supported by the supporting part and positioned in the second position of the housing after the liquid leaks from the container.
Figure 4B:
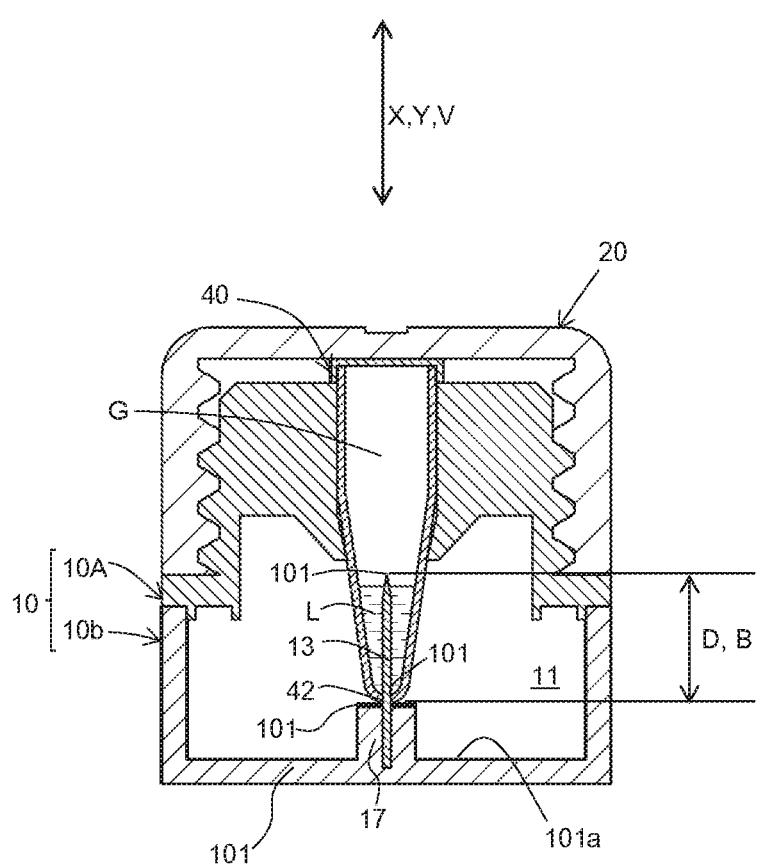
FIG. 4B schematically shows an end plane of the test device according to one or more embodiments of the present invention including a container in a short-width direction in which the container is supported by the supporting part and positioned in the second position of the housing before the liquid leaks from the container.
Figure 4C:
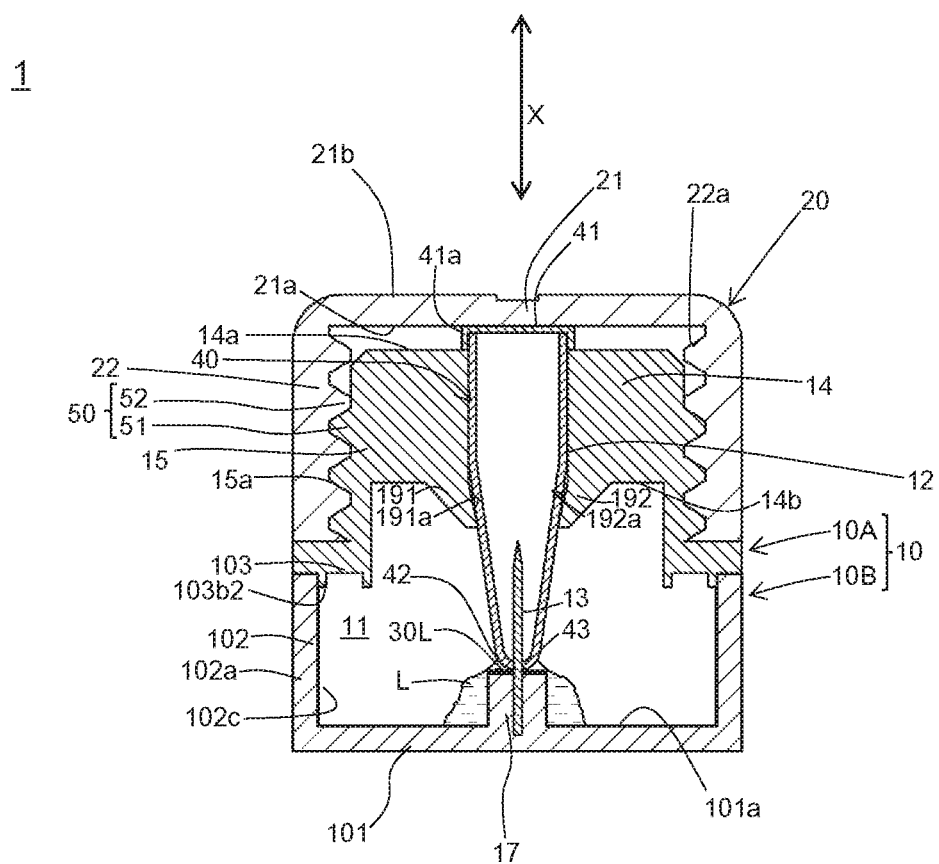
FIG. 4C schematically shows an end plane of the test device according to one or more embodiments of the present invention including a container in a short-width direction in which the container is supported by the supporting part and positioned in the second position of the housing after the liquid leaks from the container.

The conditions in which the containers 40 supported by the holes 12 of the supporting part 14 and positioned in the first position are pushed toward the blade 13 and allowed to completely migrate to the position where the inner ends 42 of the containers 40 abut against the fixing parts 17 of the housing 10 are shown in FIG. 3B and FIG. 4B (the condition before liquid L leaks) and in FIG. 3C and FIG. 4C (the condition after liquid L leaks). In this case, the containers 40 are incised by the blade 13 from the inner ends 42 of the containers 40. The position where the container is supported by the supporting part, guided by the container guide, and allowed to migrate to the position where the container is incised by the blade is defined as "the second position." As shown in FIG. 3B, FIG. 3C, FIG. 4B, and FIG. 4C, according to one or more embodiments, the container in the second position abuts against a part of the housing other than the blade.

When the containers 40 supported by the holes 12 of the supporting part 14 are guided from the first position to the second position, the containers 40 are incised by the blade 13, the incisions (leakage ports) 43 are formed on the containers 40, and liquid L accommodated in the containers 40 leaks through the incisions 43 to the position where the liquid comes into contact with the liquid contact part 30L of the chromatography support 30. An opening that is formed on the container when the container is perforated or incised by the perforation/incision part is referred to as a "leakage port" herein. When a blade serves as a perforation/incision part, in particular, a "leakage port" that is formed when the container is incised by the blade may be referred to as an "incision."

According to one or more embodiments, in addition, the liquid contact part 30L of the chromatography support 30 is accommodated in the housing 10 to be positioned between the supporting part 14 and the edge 131 of the blade 13. Thus, the container 40 is incised by the blade 13 together with the chromatography support 30. When the container 40 is in the first position, the inner end 42 of the container 40 faces the edge 131 of the blade 13 through the liquid contact part 30L of the chromatography support 30. When the container 40 supported by the supporting part 14 is guided to migrate from the first position to the second position, the container 40 is incised by the blade 13 together with the liquid contact part 30L of the chromatography support 30 from the inner end 42, and the incisions 43 are then formed. According to one or more embodiments, liquid L leaked from the container 40 easily comes into contact with the liquid contact part 30L of the chromatography support 30 and penetrates there through. The test device 1 provided with such features is capable of allowing the liquid L leaked from the container 40 to efficiently come into contact with the chromatography support 30.

According to one or more embodiments, as shown in FIG. 3A and FIG. 4A, the container 40 is supported by the supporting part 14 of the housing 10 and positioned in the first position. In this state, the lid 20 is mounted on the lid-mounting part 15 surrounding the supporting part 14 of the housing 10. In this case, the housing-side screw-engagement part 51 on the outer peripheral surface 15a of the lid-mounting part 15 of the housing 10 is partially engaged with the lid-side screw-engagement part 52 on the inner peripheral surface 22a of the peripheral wall part 22 of the lid 20. Thus, the supporting part 14 of the housing 10 and the outer region 40a of the container 40 are covered by the lid 20. Subsequently, the lid 20 is allowed to revolve around an axis in a direction X in which the supporting part 14 of the housing 10 faces the lid 20, and the lid 20 is guided by the lid guide 50 to migrate toward the supporting part 14 of the housing 10 in the direction X. During migration, the main lid part 21 of the lid 20 abuts against the outer end 41 of the container 40, and the container 40 is pushed toward the blade 13 to reach the second position shown in FIG. 3B, FIG. 3C, FIG. 4B, and FIG. 4C.

According to one or more embodiments of the present invention, the test device does not comprise the lid. In such test device, for example, the container without a lid may be supported by the supporting part of the housing. A user pushes such container with fingers from the outside of the housing or operates an apparatus or the like from the outside. Thus, the container migrates from the first position to the second position.

A Feature of the Test Device According to One or More Embodiments of the Present Invention According to the first feature of the test device 1 according to one or more embodiments of the present invention, when the length in a direction in which the containers 40 supported by the supporting part are guided by the holes 12 (i.e., the guide direction Y) is designated "M," and the maximal length of the incisions 43 formed on the containers 40 in the direction Y in which the containers 40 are supported by the supporting part 14 and guided from the first position to the second position is designated "D,"

D/M is 0.2 or greater.

The effects attained by the first feature are described with reference to FIGS. 7A-7F.

Figure 7A:
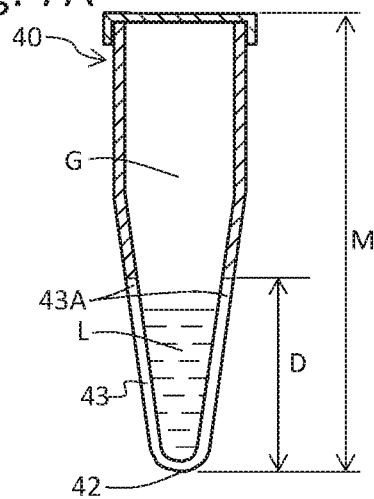
FIGS. 7A-7F illustrates the correlation between the length of the incision formed by the blade on the container and the amount of the liquid in the container. 7A and 7B show the incision of Example 1, 7C and 7D show the incision of Comparative Example 1, and 7E and 7F show the incision of Example 2.
Figure 7B:
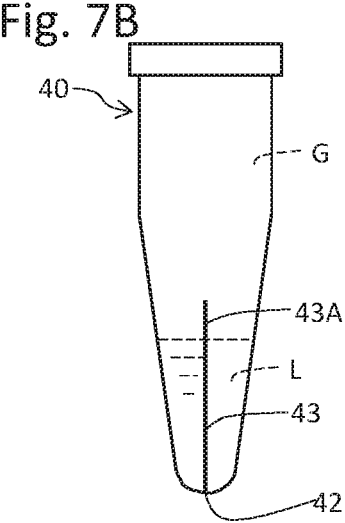
Figure 7C:
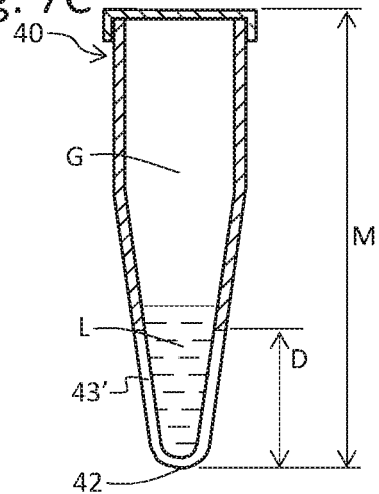
Figure 7D:
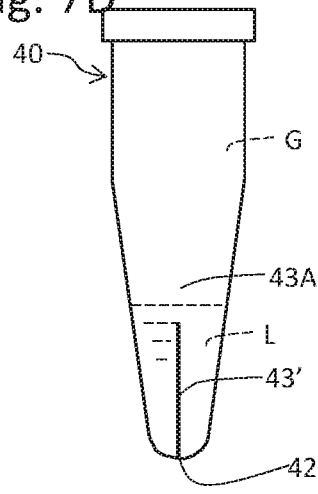

FIG. 7C schematically shows a cross section of the container 40 for illustrating difficulty of leaking liquid L from the container 40 when the incision 43 is formed in a region surrounding the liquid phase L from the inner end 42 of the container 40. FIG. 7D shows a lateral view of the container 40 shown in FIG. 7C observed from the left side. The container provided with the incision 43 in a region surrounding the liquid phase L shown in FIGS. 7C and D is referred to as "Comparative Example 1" for the convenience of description. In the container 40 of Comparative Example 1, the container 40 with a length M along the guiding direction Y accommodates liquid L to the level that is less than 0.2 M from the inner end 42, the remaining part in the container 40 is composed of the gas phase G, and the incision 43 of the maximal length D along the guiding direction Y is formed from the inner end 42 of the container 40. In Comparative Example 1, the distance from the inner end 42 to the liquid surface of liquid L of the container 40 in the vertical direction is greater than the maximal length D of the incision 43, provided that the container 40 is supported to adjust the guiding direction Y to be vertical and position the inner end 42 downward in the vertical direction. In Comparative Example 1, the container 40 is supported to adjust the guiding direction Y to be vertical and position the inner end 42 downward in the vertical direction, and the incision 43 is present in a region surrounding the liquid phase L of the container 40. When liquid L begins to leak from the container 40 to the outside thereof through the incision 43, in Comparative Example 1, the gas phase G is more likely to create a negative pressure, and it is difficult that liquid L leaks from the container 40 through the incision 43. When the container 40 is a microtube, in general, there is no vent except for the incision 43.

FIG. 7A schematically shows a cross section of the container 40 on which the incision 43 is formed from the inner end 42 shown in FIG. 3B and FIG. 4B when the container 40 is supported by the supporting part 14 of the housing 10 and allowed to migrate from the first position to the second position using the test device 1 of one or more embodiments having the first feature. FIG. 7B shows a lateral view of the container 40 shown in FIG. 7A observed from the left side. The container provided with the incision 43 shown in FIGS. 7A and 7B is referred to as "Example 1" for the convenience of description. In the container 40 of Example 1, the container 40 with a length M along the guiding direction Y accommodates liquid L to the level that is less than D from the inner end 42, the remaining part in the container 40 is composed of the gas phase G, and an incision of the maximal length D along the guiding direction Y is formed from the inner end 42 of the container 40. Since D is 0.2 M or greater, the container 40 may be supported to adjust the guiding direction Y to be vertical and position the inner end 42 downward in the vertical direction. Thus, two upper edges 43A of the incision 43 are positioned in a region surrounding the gas phase G of the container 40, and it allows the gas phase G inside the container 40 to communicate with the external air. When liquid L begins to leak from the container 40 to the outside thereof through the incision 43, air is supplied to the gas phase G from the outside of the container through the upper edges 43A of the incision 43, the gas phase G is less likely to create a negative pressure, and liquid L can smoothly leak from the container 40 through the incision 43. To this end, liquid L can be accommodated in the container to the depth of less than D; that is, to the depth of at least less than 0.2 M.

Figure 7E:
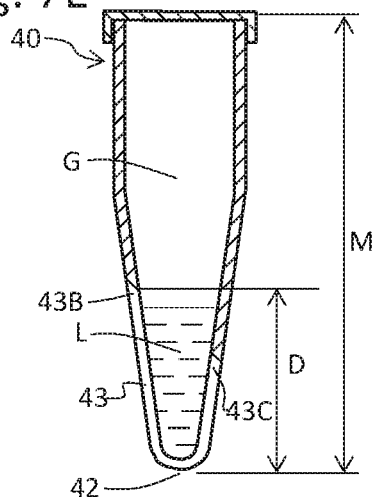
Figure 7F:
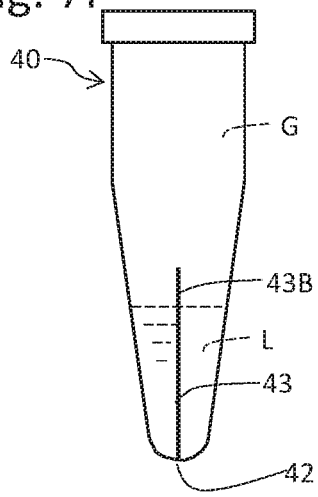

In the test device 1 according to one or more embodiments shown in the figure, the edge 131 of the blade 13 extends in a line and it is positioned to become orthogonal to the guiding direction Y. Thus, the incision 43 formed on the container 40 is configured to be of a symmetrical U-shape as with the case of Example 1, although the test device is not limited to one or more embodiments. For example, FIG. 7E schematically shows a cross section of the container 40 on which the incision 43 is formed from the inner end 42 when the container 40 is supported by the supporting part 14 of the housing 10 and allowed to migrate from the first position to the second position using the test device 1 having the structure similar to that according to one or more embodiments shown in the figure, except that the edge 131 of the blade 13 extends in a line and it is positioned to incline with respect to the guiding direction Y. FIG. 7F shows a lateral view of the container 40 shown in FIG. 7E observed from the left side. The container 40 provided with the incision 43 shown in FIGS. 7E and 7F is referred to as "Example 2" for the convenience of description. In the container 40 of Example 2, the container 40 with a length M along the guiding direction Y accommodates liquid L to the level that is less than D from the inner end 42, the remaining part in the container 40 is composed of the gas phase G, and the incision of the maximal length D along the guiding direction Y is formed from the inner end 42 of the container 40. In this case, D is 0.2 M or greater. In Example 2, the incision 43 is not symmetrical. When the container 40 is supported to adjust the guiding direction Y to be vertical and position the inner end 42 downward in the vertical direction, one upper edge 43B of the incision 43 is positioned upward from the other upper edge 43C in the vertical direction. The maximal length D is a length of the incision 43 from the inner end 42 to the upper edge 43B in the guiding direction Y. The container 40 of Example 2 may be supported to adjust the guiding direction Y to be vertical and position the inner end 42 downward in the vertical direction. Thus, the upper edge 43B of the incision 43 is positioned in a region surrounding the gas phase G of the container 40, and it allows the gas phase G inside the container 40 to communicate with the external air. When liquid L begins to leak from the container 40 to the outside thereof through the incision 43, air is supplied to the gas phase G from the outside of the container through the upper edge 43B of the incision 43, the gas phase G is less likely to create a negative pressure, and liquid L can smoothly leak from the container 40 through the incision 43.

Specifically, the containers 40 that accommodate liquid L to the level that is less than D at one end with the remaining part therein being composed of the gas phase G is supported by the supporting part 14 of the test device 1 having the first feature according to one or more embodiments of the present invention, such that D/M is 0.2 or greater, to position the one of the ends to face downward in the vertical direction and adjust the guiding direction Y to become approximately vertical, and the container 40 is guided from the first position to the second position. As a result, the blade 13 forms the incisions 43 on the container 40 that reach a region surrounding the gas phase G. In this case, air is supplied to the gas phase G from the outside of the container through the region of the incision 43 formed on the container 40 that communicates the gas phase G with the outside of the container. When liquid L begins to leak from the container 40 through the incision 43, accordingly, the gas phase G is less likely to create a negative pressure, and liquid L can smoothly leak from the container 40.

According to the first feature, D/M is 0.2 or greater, 0.3 or greater, and 0.4 or greater. While the upper limit of D/M is not particularly limited, it is generally 0.9 or less.

A Feature of the Test Device According to One or More Embodiments of the Present Invention According to the second feature of the test device 1 according to one or more embodiments of the present invention, when the container 40 is supported by the supporting part 14 of the housing 10 in the first position in a manner such that liquid L is positioned at the inner end 42 of the container 40 facing the edge 131 of the blade 13, the distance in the vertical direction from the inner end 42 of the container 40 to the part 40L1 of the container 40 that is the liquid surface L1 when the container 40 accommodates liquid L is designated as A, and when the container 40 is guided from the first position to the second position, the maximal length of the incisions 43 formed on the container 40 in the vertical direction is designated as B, B is greater than A.

Specifically, the distance A can be a distance from the end of the container to the surface of the liquid accommodated in the container in a vertical direction when the container is supported by the supporting part to allow the end of the container to face downward in the vertical direction in the first position. When "the end of the container faces downward in the vertical direction," the container is supported by the supporting part in a manner such that the end is located downward with respect to the other end, so that the liquid is positioned at the end of the container. According to one or more embodiments described in Examples 3 and 4 below, the container is supported in a manner such that the longitudinal direction of the container becomes substantially vertical. According to one or more embodiments described in Example 5 below, the container is supported in a manner such that the longitudinal direction of the container inclines with respect to the vertical direction. The maximal length B of the incision can be the maximal length of the incision formed on the container in a vertical direction when the container is guided from the first position to the second position.

The effects attained by the second feature are described with reference to FIGS. 8A-8F and FIG. 8G.

Figure 8A:
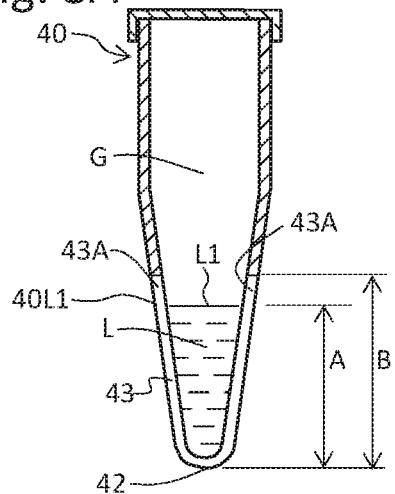
FIGS. 8A-8F illustrates the correlation between the length of the incision formed by the blade on the container and the amount of the liquid in the container. 8A and 8B show the incision of Example 3, 8C and 8D show the incision of Comparative Example 2, and 8E and 8F show the incision of Example 4.
Figure 8B:
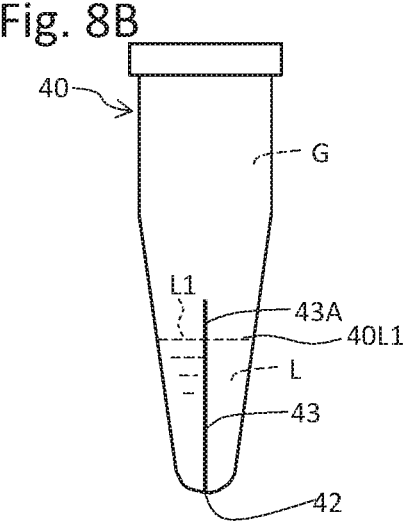
Figure 8C:
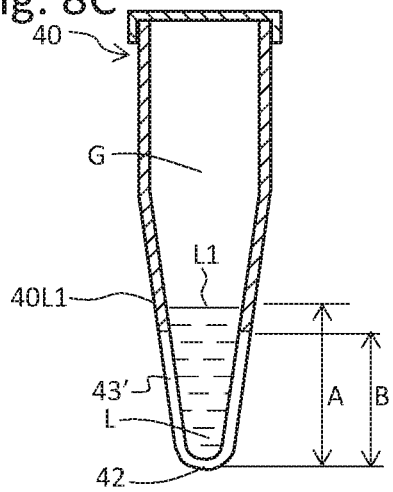
Figure 8D:
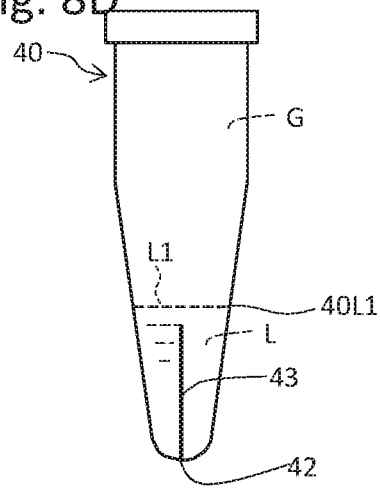

FIG. 8C schematically shows a cross section of the container 40 on which the incision 43 of the maximal length B (not greater than A) in the vertical direction V is formed when the container 40 accommodating liquid L and the gas phase G is supported by the supporting part 14 of the housing 10 and allowed to migrate from the first position to the second position with the use of a test device with the feature similar to that of the test device 1 with the second feature of one or more embodiments of the present invention, except that B is not greater than A. FIG. 8D shows a lateral view of the container 40 shown in FIG. 8C observed from the left side. The container 40 provided with the incision 43 with the maximal length B of not greater than A in the vertical direction V shown in FIGS. 8C and 8D is referred to as "Comparative Example 2" for the convenience of description. When the container 40 of Comparative Example 2 is in the second position in the test device, the incision 43 is present in a region of the container 40 surrounding the liquid phase L. When liquid L begins to leak from the container 40 through the incision 43, accordingly, the gas phase G is more likely to create a negative pressure, and it is difficult that liquid L leaks from the container 40 through the incision 43.

FIG. 8A schematically shows a cross section of the container 40 on which the incision 43 of the maximal length B (greater than A) in the vertical direction V is formed when the container 40 is supported by the supporting part 14 of the housing 10 and allowed to migrate from the first position to the second position with the use of the test device 1 with the second feature of one or more embodiments of the present invention. FIG. 8B shows a lateral view of the container 40 shown in FIG. 8A observed from the left side. The container 40 provided with the incision 43 with the maximal length B of greater than A in the vertical direction V shown in FIGS. 8A and 8B is referred to as "Example 3" for the convenience of description. When the container 40 of Example 3 is in the second position in the test device 1 according to one or more embodiments, two upper edges 43A of the incision 43 are positioned in a region surrounding the gas phase G of the container 40, and it allows the gas phase G inside the container 40 to communicate with the external air. When liquid L begins to leak from the container 40 to the outside thereof through the incision 43, air is supplied to the gas phase G from the outside of the container through the upper edges 43A of the incision 43, the gas phase G is less likely to create a negative pressure, and liquid L can smoothly leak from the container 40 through the incision 43.

Figure 8E:
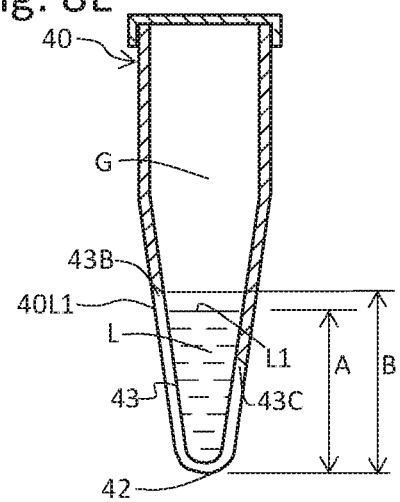
Figure 8F:
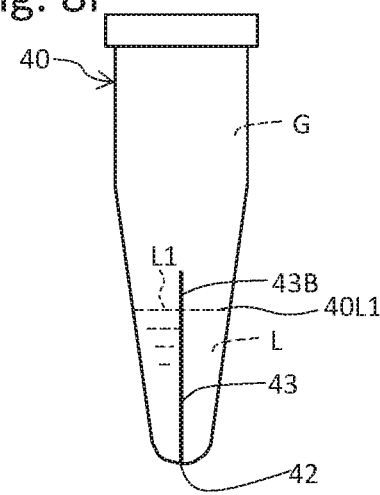
Figure 8G:
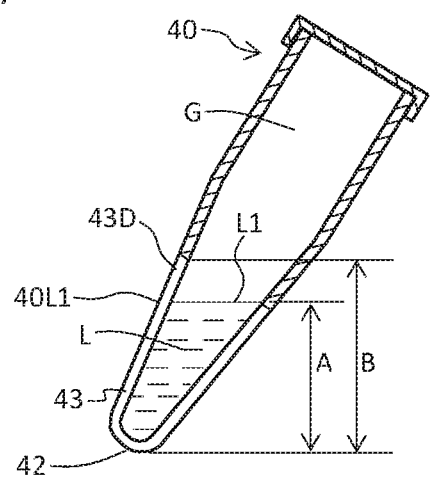
FIG. 8G is a continuation from FIGS. 8A-8F, and 8G shows the incision of Example 5.
Figure 10A:
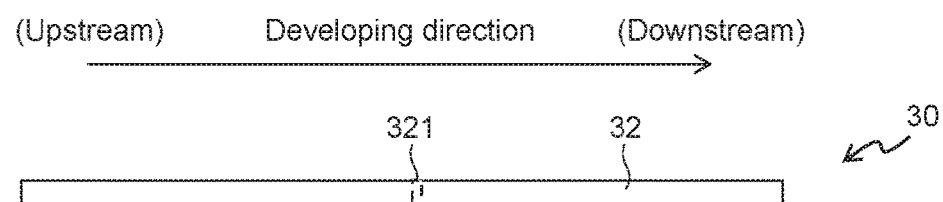
FIG. 10 shows a structure of another chromatography support that can be used in one or more embodiments of the present invention. 10A shows a plane view, and 10B shows a lateral view.
Figure 10B:
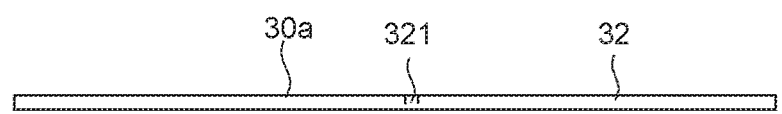

FIG. 8E schematically shows a cross section of the container 40 on which the incision 43 of the maximal length B (greater than A) in the vertical direction V is formed when the container 40 is supported by the supporting part 14 of the housing 10 and allowed to migrate from the first position to the second position with the use of the test device 1 of the structure similar to that according to one or more embodiments shown in the figure, except that the edge 131 of the blade 13 extends in a line and it is positioned to incline with respect to the guiding direction Y. FIG. 8F shows a lateral view of the container 40 shown in FIG. 8E observed from the left side. The container 40 provided with the incision 43 with the maximal length B of greater than A in the vertical direction V shown in FIGS. 8E and 8F are referred to as "Example 4" for the convenience of description. When the container 40 of Example 4 is in the second position in the test device 1 according to one or more embodiments, one upper edge 43B of the incision 43 is positioned upward from the other upper edge 43C in the vertical direction, and such upper edge 43B of the incision 43 is positioned in a region surrounding the air phase G of the container 40. This allows the gas phase G inside the container 40 to communicate with the external air. When liquid L leaks from the container 40 to the outside of the container through the incision 43, air is supplied to the gas phase G from the outside of the container through the upper edge 43B of the incision 43, the gas phase G is less likely to create a negative pressure, and liquid L can smoothly leak from the container 40 through the incision 43.

According to Example 3 shown in FIG. 8A and Example 4 shown in FIG. 8E, the longitudinal direction of the container 40 is substantially vertical when the container 40 is supported by the supporting part 14 of the housing 10. In the test device 1 with the second feature of one or more embodiments of the present invention, however, the longitudinal direction of the container 40 is not necessarily vertical when the container 40 is supported by the supporting part 14, and it may incline with respect to the vertical direction. For example, FIG. 8G (7) schematically shows a cross section of the container 40 on which the incision 43 of the maximal length B (greater than A) in the vertical direction V is formed when the container 40 is supported by the supporting part 14 of the housing 10 and allowed to migrate from the first position to the second position with the use of the test device 1 with one or more embodiments of the present invention having the structure similar to that according to one or more embodiments shown in FIG. 1A to FIG. 4C, except that the container is supported by the supporting part 14 of the housing 10 to allow the longitudinal direction of the container 40 to incline with respect to the vertical direction, the container 40 is guided from the first position to the second position, and the blade 13 forms the incision 43 of the configuration as shown in the figure on the container 40. The container 40 shown in FIG. 8G (7) that is provided with the incision 43 with the maximal length B of greater than the distance A in the vertical direction V, which is a distance from the inner end 42 of the container 40 to the part 40L1 of the container 40 where the liquid surface L1 is present, is referred to as "Example 5" for the convenience of description. When the container 40 of Example 5 is in the second position in the test device 1 according to one or more embodiments, one upper edge 43D of the incision 43, which is positioned upward in a vertical direction V from the other upper edge of the incision, is positioned in a region surrounding the air phase G of the container 40, and it allows the gas phase G inside the container 40 to communicate with the external air. When liquid L begins to leak from the container 40 to the outside thereof through the incision 43, air is supplied to the gas phase G from the outside of the container through the upper edge 43D of the incision 43, the gas phase G is less likely to create a negative pressure, and liquid L can smoothly leak from the container 40 through the incision 43.

When the step 1 of allowing the supporting part 14 of the test device 1 with the second feature of one or more embodiments of the present invention; i.e., B is greater than A, to support the container 40 that accommodates the liquid L and the gas phase G in a manner such that the liquid L is positioned at an inner end 42 of the container 40 in the first position therein, and the subsequent step 2 of guiding the container 40 from the first position to the second position are carried out, the blade 13 forms the incision 43 that reaches a region surrounding the gas phase G on the container 40. In such a case, air is supplied to the gas phase G from the outside of the container through the part of the container 40 that communicates the gas phase G to the outside of the container. When liquid L begins to leak from the containers 40 through the incisions 43, accordingly, the gas phase G is less likely to create a negative pressure, and liquid L can smoothly leak from the containers 40.

Figure 5A:
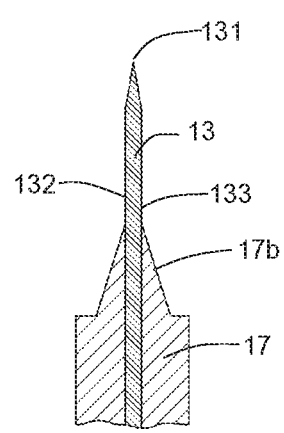
FIG. 5A schematically shows a cross section of one or more embodiments of a fixing part with a tapered end for fixing the blade to the housing in a blade thickness direction.

One or More Embodiments of the Fixing Part According to One or More Embodiments the Present Invention According to a variation example of the test device 1 according to one or more embodiments of the present invention, the fixing part 17 that fixes the blade 13 has the structure as shown in FIG. 5A.

The fixing part 17 shown in FIG. 5A is provided with a tapered end 17b that makes the dimension of the fixing part 17 in a thickness direction of the blade 13 to become smaller toward the edge 131 of the blade 13.

Figure 5B:
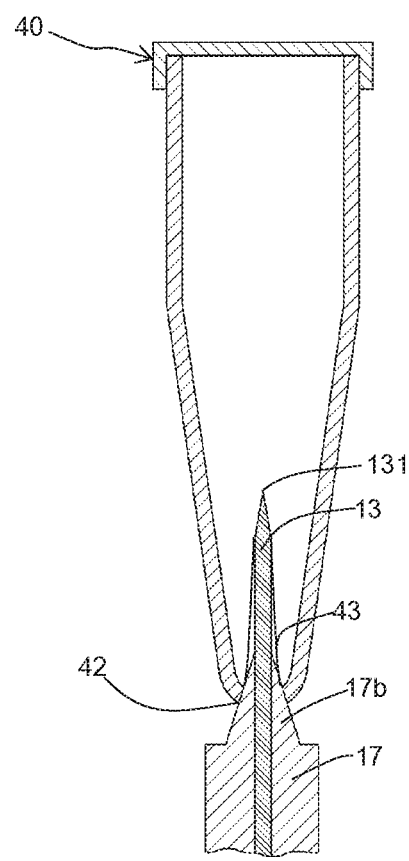
FIG. 5B schematically shows a cross section of the container pushed toward the blade fixed by the fixing part with a tapered end shown in FIG. 5A until the tapered end is inserted into the incision in a blade thickness direction.

When the container 40 is supported by the supporting part 14 and guided from the first position to the second position with the use of a variation example of the test device 1 according to one or more embodiments of the present invention that comprises the fixing part 17 with the tapered end 17b, as shown in FIG. 5B, the tapered end 17b of the fixing part 17 is inserted into the incision 43 formed on the container 40. As a result, an opening width of the incision 43 is expanded, and the liquid L accommodated in the container 40 can leak from the container through the incision 43 more smoothly.

Figure 6A:
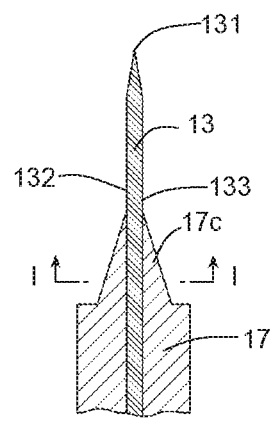
FIG. 6A schematically shows a cross section of a fixing part with a tapered end for fixing the blade to the housing according to one or more embodiments in a blade thickness direction.
Figure 6B:
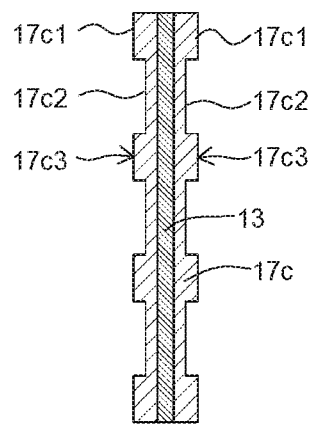
FIG. 6B schematically shows a cross section of the fixing part shown in FIG. 6A taken along the I-I line.

According to variation example of one or more embodiments of the test device 1 according to one or more embodiments of the present invention, the fixing part 17 that fixes the blade 13 has the structure shown in FIG. 6A and FIG. 6B.

The fixing part 17 shown in FIG. 6A comprises the tapered end 17c that makes the dimension of the fixing part 17 in a thickness direction of the blade 13 to become smaller toward the edge 131 of the blade 13. FIG. 6B shows a cross section of the tapered end 17c shown in FIG. 6A taken along the I-I line. As shown in FIG. 6B, the tapered end 17c has, as a lateral surface, a concave-convex surface 17c3 with a region 17c1 protruded in a thickness direction of the blade 13 and a region 17c2 recessed in a thickness direction of the blade 13.

When the container 40 is supported by the supporting part 14 and guided from the first position to the second position with the use of a variation example of the test device 1 according to one or more embodiments of the present invention that comprises the fixing part 17 with the tapered end 17c, the tapered end 17c of the fixing part 17 is inserted into the incision 43 formed on the container 40. As a result, an opening width of the incision 43 is expanded, and the liquid L accommodated in the container 40 can leak from the container through the incision 43 more smoothly. In addition, gaps are formed between the end surface of the incision 43 formed on the container 40 and the concave-convex surface 17c3 of the tapered end 17c, and the liquid L can leak from the container through the incision 43 more smoothly.

Subsequently, features of one or more embodiments of the present invention are described.

With reference to FIG. 11A to FIG. 12B, the mechanism of perforating or incising the containers 40 inserted into the holes 12 of the supporting part 14 and supported thereby and the chromatography support 30 by the perforation/incision part 13 is described.

Figure 11A:
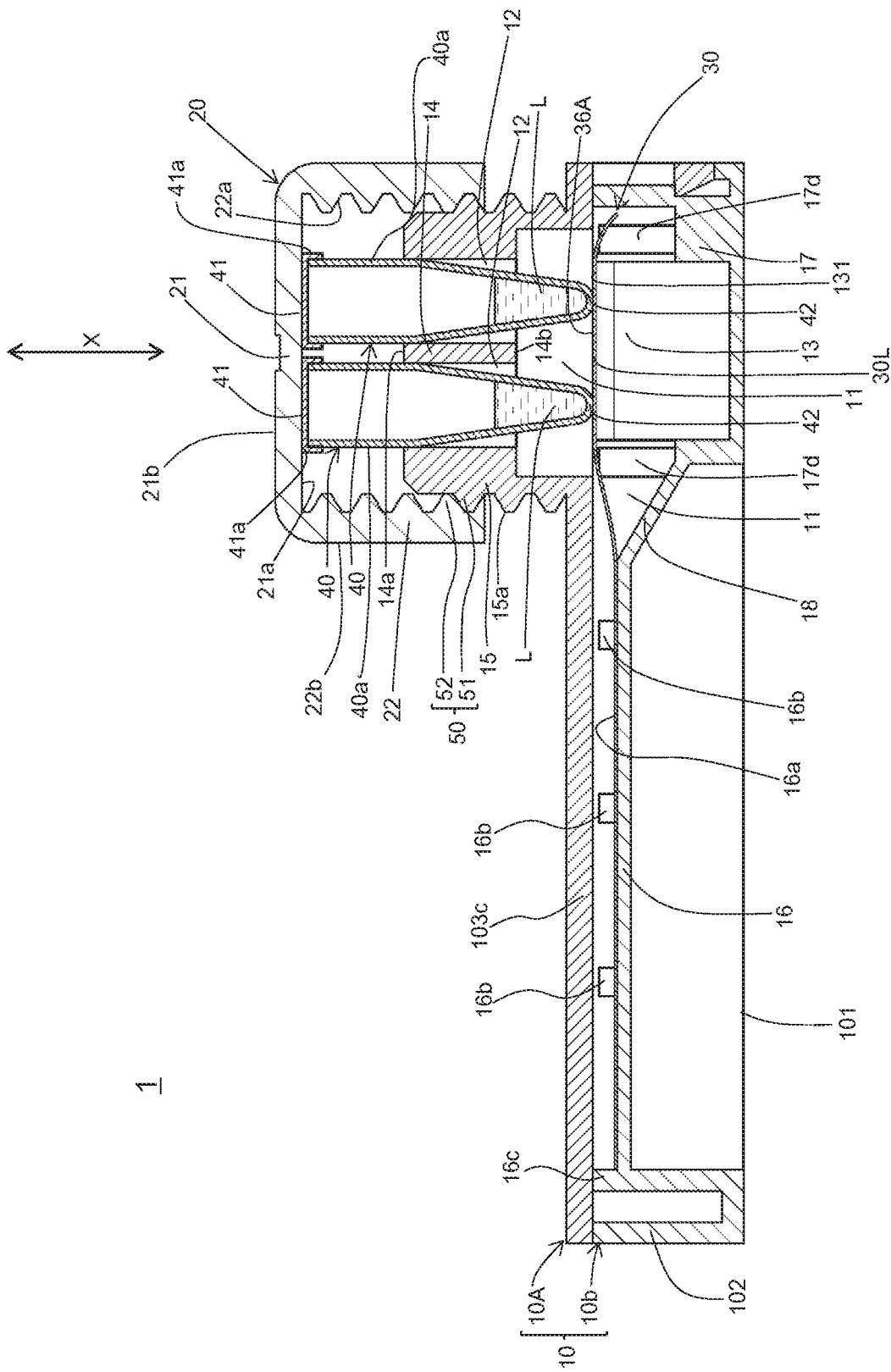
FIG. 11A schematically shows a cross section of the test device according to one or more embodiments of the present invention in a longitudinal direction in which the container is supported by the supporting part and positioned in the first position of the housing.
Figure 12A:
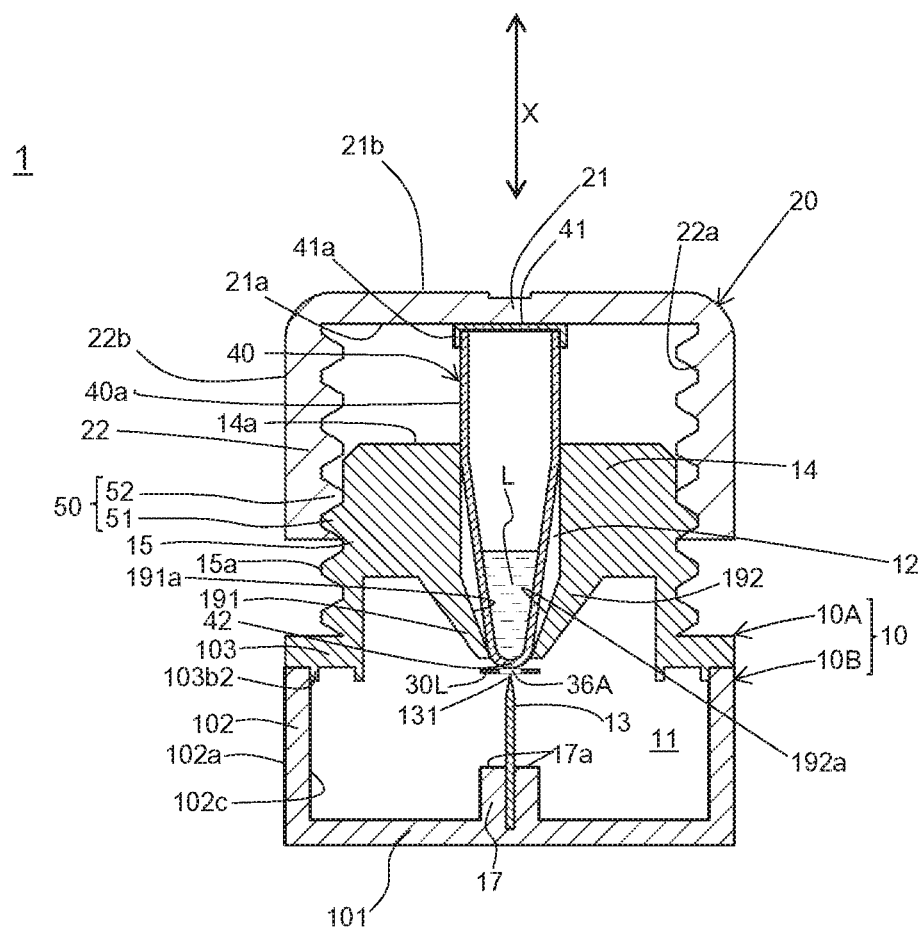
FIG. 12A schematically shows an end plane of the test device according to one or more embodiments of the present invention including a container in a short-width direction in which the container is supported by the supporting part and positioned in the first position of the housing.

FIG. 11A and FIG. 12A each show the container 40 accommodating liquid L that is inserted into the holes 12 of the supporting part 14 and supported thereby. The inner end 42 of the container 40 faces the edge 131 of the blade 13. The position where the container is supported by the supporting part with one end of the container facing the perforation/incision part is defined as "the first position."

Figure 11B:
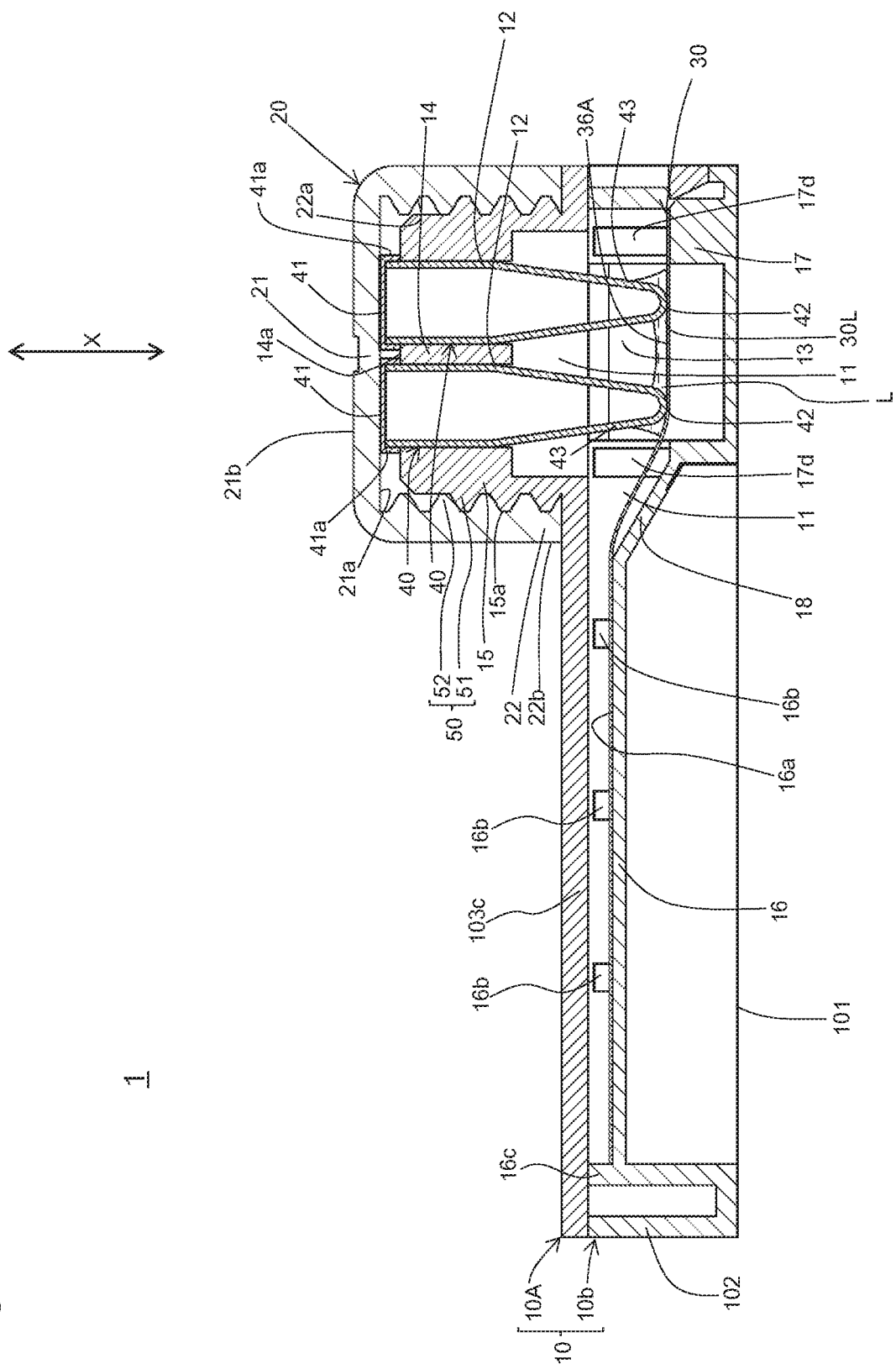
FIG. 11B schematically shows a cross section of the test device according to one or more embodiments of the present invention in a longitudinal direction in which the container is supported by the supporting part and positioned in the second position of the housing.
Figure 12B:
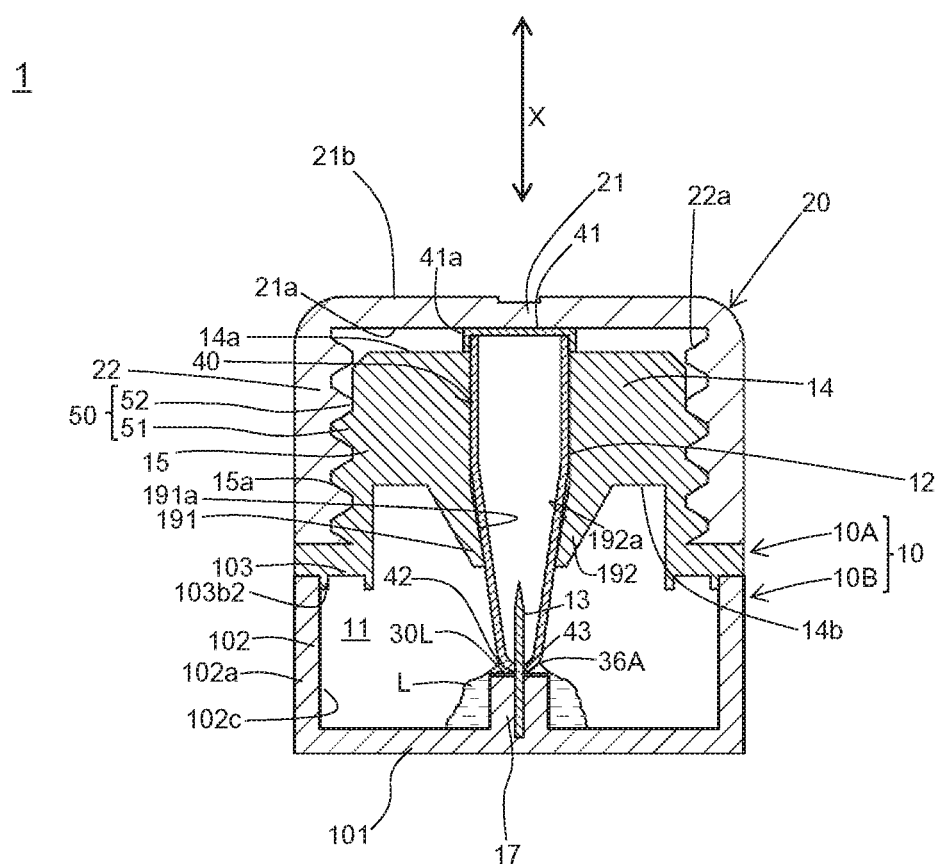
FIG. 12B schematically shows an end plane of the test device according to one or more embodiments of the present invention including a container in a short-width direction in which the container is supported by the supporting part and positioned in the second position of the housing.

FIG. 11B and FIG. 12B each show the containers 40 supported by the holes 12 of the supporting part 14 and positioned in the first position that are pushed toward the perforation/incision part 13 and allowed to completely migrate to the position where the inner ends 42 of the containers 40 abut against the fixing parts 17 of the housing 10. In this case, the containers 40 are incised by the blade 13 from the inner ends 42 of the containers 40. The position where the container is supported by the supporting part, guided by the container guide, and allowed to migrate to the position where the container is perforated or incised by the perforation/incision part is defined as "the second position." As shown in FIG. 11B and FIG. 12B, according to one or more embodiments, the container in the second position abuts against a part of the housing other than the perforation/incision part.

While the container 40 supported by the hole 12 of the supporting part 14 is guided from the first position to the second position, the container 40 is perforated or incised by the perforation/incision part 13, and liquid L accommodated in the container 40 leaks to the position where the liquid comes into contact with the liquid contact part 30L of the chromatography support 30. The container 40 is perforated or incised by the perforation/incision part 13, and the leakage port 43 is then formed thereon. From the container 40 comprising the leakage port 43 formed thereon, the liquid L accommodated therein leaks through the leakage port 43 into the internal space 11, and the liquid comes into contact with, in addition to the liquid contact part 30L of the chromatography support 30, a part of the housing 10 including the perforation/incision part 13 and the bottom wall 101 (the fixing part 17, in particular) in the vicinity of the liquid contact part 30L. An opening that is formed on the container when the container is perforated or incised by the perforation/incision part is referred to as a "leakage port" herein. When a blade serves as a perforation/incision part, in particular, a "leakage port" that is formed when the container is incised by the blade may be referred to as an "incision."

According to one or more embodiments, in addition, the liquid contact part 30L of the chromatography support 30 is accommodated in the housing 10 in a position between the supporting part 14 and the perforation/incision part 13. Thus, the container 40 is incised by the perforation/incision part 13 together with the chromatography support 30. When the container 40 is in the first position, the inner end 42 of the container 40 faces the perforation/incision part 13 through the liquid contact part 30L of the chromatography support 30. When the container 40 supported by the supporting part 14 is guided to migrate from the first position to the second position, the container 40 is perforated or incised by the perforation/incision part 13 together with the liquid contact part 30L of the chromatography support 30. According to one or more embodiments, liquid L leaked from the container 40 easily comes into contact with the liquid contact part 30L of the chromatography support 30 and penetrates there through. The test device 1 provided with such features is capable of allowing the liquid L leaked from the container 40 to efficiently come into contact with the chromatography support 30.

According to one or more embodiments, as shown in FIG. 11A and FIG. 12A, the container 40 is supported by the supporting part 14 of the housing 10 and positioned in the first position. In this state, the lid 20 is mounted on the lid-mounting part 15 surrounding the supporting part 14 of the housing 10. In this case, the housing-side screw-engagement part 51 on the outer peripheral surface 15a of the lid-mounting part 15 of the housing 10 is partially engaged with the lid-side screw-engagement part 52 on the inner peripheral surface 22a of the peripheral wall part 22 of the lid 20. Thus, the supporting part 14 of the housing 10 and the outer region 40a of the container 40 are covered by the lid 20. Subsequently, the lid 20 is allowed to revolve around an axis in a direction X in which the supporting part 14 of the housing 10 faces the lid 20, and the lid 20 is guided by the lid guide 50 to migrate toward the supporting part 14 of the housing 10 in the direction X. During migration, the main lid part 21 of the lid 20 abuts against the outer end 41 of the container 40, and the container 40 is pushed toward the perforation/incision part 13 to reach the second position shown in FIG. 11B and FIG. 12B. When the lid 20 is allowed to revolve around an axis in the direction X in which the supporting part 14 of the housing 10 faces the lid 20, the container 40 is pushed toward the perforation/incision part 13 with a slight inclination from the direction X as the lid 20 revolves. Thus, the leakage port 43 formed on the container 40 as a result of perforation or incision becomes open, liquid L efficiently leaks therefrom, and chromatography conditions can be stabilized.

According to one or more embodiments of the present invention, the test device does not necessarily comprise the lid as required in one or more embodiments. In such test device, for example, the container without a lid may be supported by the supporting part of the housing. A user pushes such container with fingers from the outside of the housing or operates an apparatus or the like from the outside. Thus, the container migrates from the first position to the second position.

The test device 1 of one or more embodiments comprises, in a position on the chromatography support 30 that comes into contact with the perforation/incision part 13, a perforation/incision target part that is more easily to be perforated or incised by the perforation/incision part 13 than other parts of the chromatography support 30 provided thereon in advance.

In a specific example of a perforation/incision target part according to one or more embodiments shown in FIG. 11A to FIG. 12B, a slit hole 36A that penetrates through the chromatography support 30 in a thickness direction is provided in the liquid contact part 30L of the chromatography support 30. An example of the chromatography support 30 provided with the slit hole 36A is shown in FIGS. 14A-14B and FIGS. 15A-15B. The slit hole 36A has a configuration in accordance with the edge 131 of the blade 13, which is the perforation/incision part; that is, the slit hole 36A extends along the blade edge 131. When the container 40 is supported by the supporting part 14 of the housing 10 and positioned in the first position of the test device 1 according to one or more embodiments in which the chromatography support 30 comprising the slit hole 36A formed in the liquid contact part 30L is accommodated in the housing 10, as shown in FIG. 11A and FIG. 12A, the liquid contact part 30L of the chromatography support 30 is positioned between the inner end 42 of the container 40 and the edge 131 of the blade 13 facing thereto. The slit hole 36A is provided in a position of the liquid contact part 30L on chromatography support 30 that comes into contact with the edge 131 of the blade 13. Subsequently, the lid 20 is allowed to revolve around an axis in a direction X with respect to the housing 10, and the lid 20 is guided by the lid guide 50 to migrate toward the supporting part 14 of the housing 10 in the direction X. During migration, the container 40 is pushed by the main lid part 21 of the lid 20 toward the blade 13 together with the liquid contact part 30L on the chromatography support 30, and it reaches the second position shown in FIG. 11B and FIG. 12B in the end. When the container 40 migrates from the first position to the second position, according to one or more embodiments, the edge 131 of the blade 13 more easily incises the slit hole 36A compared with other parts of the chromatography support 30. Thus, the edge 131 of the blade 13 penetrates through the slit hole 36A of the chromatography support 30 and the container 40 is incised as intended. According to one or more embodiments, as described above, the slit hole 36A may be provided in advance in a position of the chromatography support 30 that comes into contact with the blade 13. When the container 40 and the chromatography support 30 are to be incised together by the blade 13, accordingly, the chromatography support 30 is less likely to be misaligned from the blade 13, and the container 40 and the chromatography support 30 can be easily incised together. When the chromatography support 30 and the container 40 are to be perforated or incised together by the blade 13, in addition, resistance caused by the chromatography support 30 is small. Compared with the use of the chromatography support 30 without the perforation/incision target part such as the slit hole 36A, accordingly, the container 40 and the chromatography support 30 can be incised together with a relatively small force.

Figure 13:
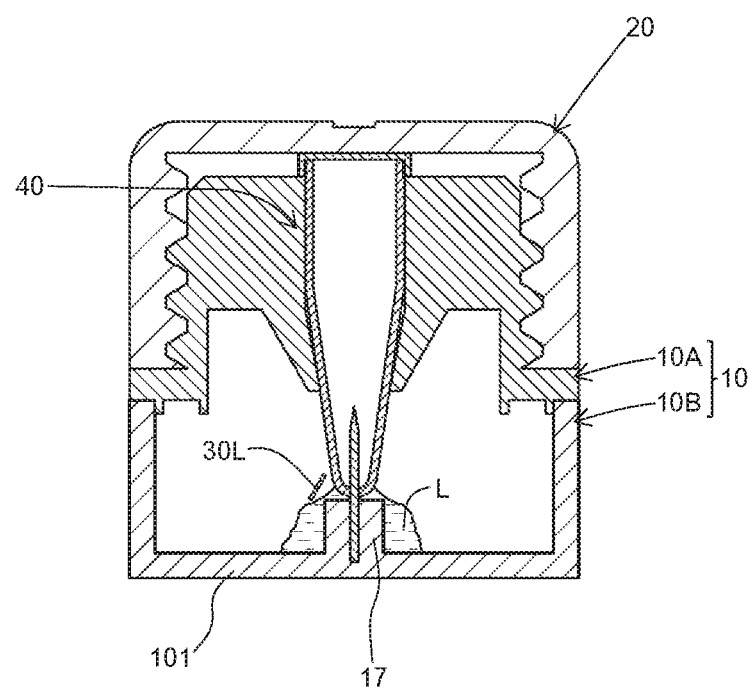
FIG. 13 schematically shows an end plane of a test device in which the chromatography support is not provided with a perforation/incision target part in advance according to a comparative example including a container in a short-width direction in which the container is supported by the supporting part and positioned in the second position of the housing.

FIG. 13 schematically shows the container 40 supported by the supporting part 14 and guided from the first position to the second position using the test device 1' of a comparative example having the structure similar to that according to one or more embodiments described above, except that a perforation/incision target part, such as the slit hole 36A, is not provided in the liquid contact part 31L of the chromatography support. In the test device 1' of the comparative example, the chromatography support 30 is easily misaligned from the blade 13 when the container 40 and the chromatography support 30 are to be incised together by the blade 13. As shown in FIG. 13, as a result, the liquid contact part 30L of the chromatography support 30 is not incised in a region as intended, but the container 40 is incised. Thus, the liquid L leaked from the container 40 may not be able to sufficiently come into contact with the liquid contact part 30L of the chromatography support 30.

According to one or more embodiments shown in FIG. 11A to FIG. 12B, the chromatography support 30 may be provided with, as a specific example of a perforation/incision target part, a slit hole 36A penetrating through the chromatography support 30 in a thickness direction (FIGS. 14A-14B and FIGS. 15A-15B). It is noted that the configuration of the perforation/incision target part is not limited thereto.

According to one or more embodiments of the present invention, a perforation/incision target part is one or more elements selected from the group consisting of:

an incision that penetrates through the chromatography support in a thickness direction;

a groove formed on a part of the chromatography support in a thickness direction;

a hole that penetrates through the chromatography support in a thickness direction; and a line of perforation comprising two or more elements selected from among the incision that penetrates through the chromatography support in a thickness direction, the groove formed on a part of the chromatography support in a thickness direction, and the hole that penetrates through the chromatography support in a thickness direction. The slit hole 36A according to one or more embodiments shown in FIG. 11A to FIG. 12B is one or more embodiments of a hole that penetrates through the chromatography support in a thickness direction.

Figure 16A:
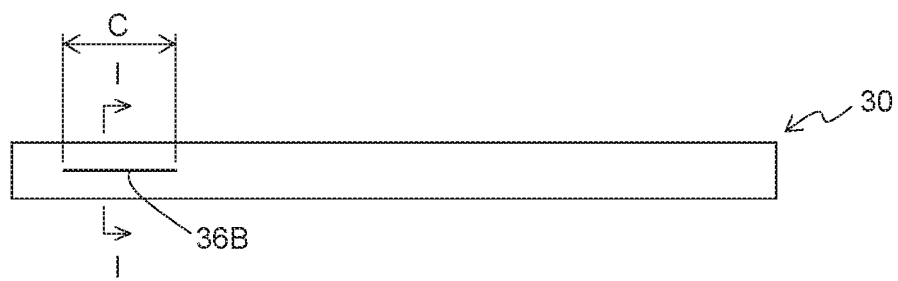
FIG. 16A-16C shows an example of a chromatography support provided with an incision as a perforation/incision target part that can be used in one or more embodiments of the present invention. 16A shows a plane view, 16B shows a cross section of 16A taken along the I-I line, and 16C shows a plane view of an example of a chromatography support provided with an incision from the end thereof.
Figure 16B:
Figure 16C:
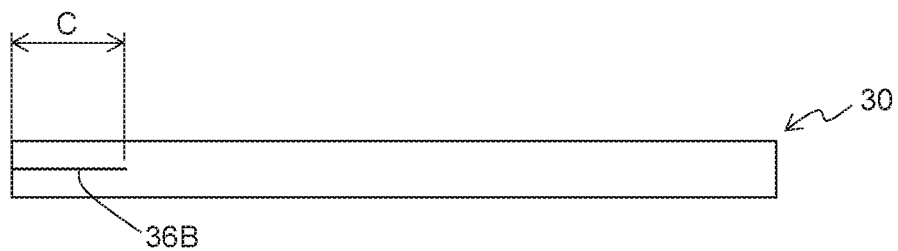

FIGS. 16A-16C shows an example of the chromatography support 30 provided with an incision 36B penetrating through the chromatography support 30 in a thickness direction in a position that comes into contact with the perforation/incision part 13. As shown in FIG. 16A, the incision 36B may be formed in a manner such that the incision 36B would be positioned inside the chromatography support 30 in its plane view. As shown in FIG. 16C, alternatively, the incision 36B may be formed from the end of the chromatography support 30. Also, a perforation/incision target part of one or more embodiments may be formed from the end of the chromatography support, although one or more embodiments thereof is not shown.

Figure 17A:
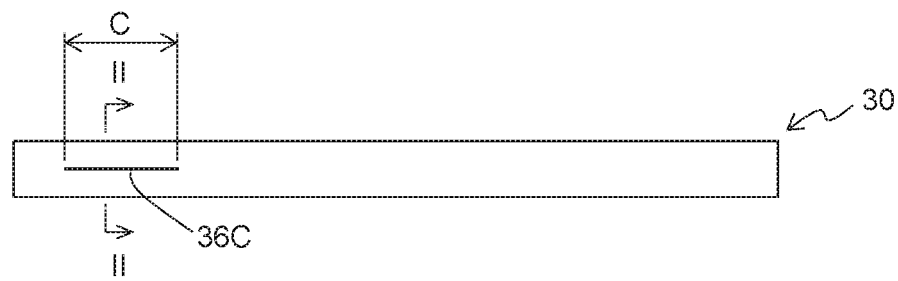
FIG. 17A-17B shows an example of a chromatography support provided with a groove with no width as a perforation/incision target part that can be used in one or more embodiments of the present invention. 17A shows a plane view, and 17B shows a cross section of 17A taken along the II-II line.
Figure 17B:
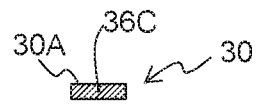

FIGS. 17A-17B shows an example of the chromatography support 30 provided with a groove 36C with no width in a part thereof in a thickness direction in a position where the chromatography support 30 comes into contact with the perforation/incision part 13.

Figure 18A:
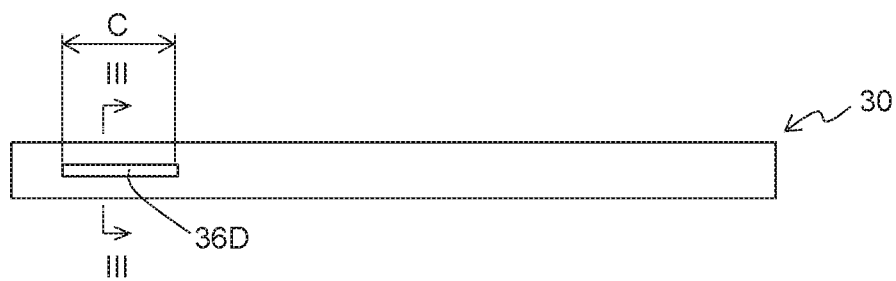
FIG. 18A-18B shows an example of a chromatography support provided with a groove with a width as a perforation/incision target part that can be used in one or more embodiments of the present invention. 18A shows a plane view, and 18B shows a cross section of 18A taken along the line.
Figure 18B:
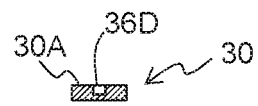

FIGS. 18A-18B shows an example of a chromatography support 30 provided with a groove 36D with a width in a part thereof in a thickness direction in a position where the chromatography support 30 comes into contact with the perforation/incision part 13.

As shown in FIGS. 17A-17B and FIGS. 18A-18D, the surface of the chromatography support 30 on which the groove 36C with no width or the groove 36D with a width is provided is referred to as the "surface 30A." The perforation/incision part 13 is provided to come into contact with the chromatography support 30 from the surface 30A from the viewpoint of prevention of misalignment.

Figure 19A:
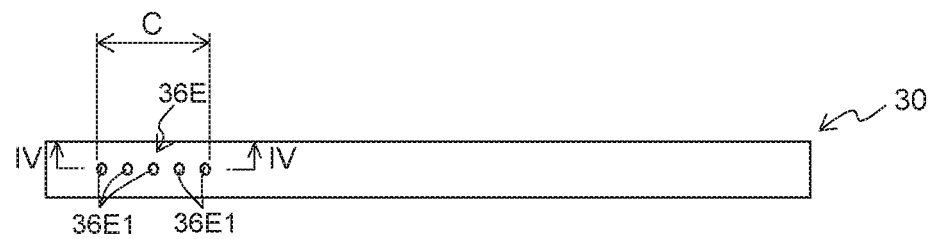
FIG. 19A-19B shows an example of a chromatography support provided with a line of perforation as a perforation/incision target part that can be used in one or more embodiments of the present invention. 19A shows a plane view, and 19B shows a cross section of 19A taken along the IV-IV line.
Figure 19B:
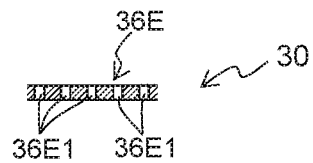

FIGS. 19A-19B show an example of a chromatography support 30 provided with a line of perforation 36E composed of 5 round holes 36E1 penetrating through the chromatography support 30 in a thickness direction in a position where the chromatography support 30 comes into contact with the perforation/incision part 13.

The length of the perforation/incision target part along the perforation/incision part (the length C shown in FIGS. 16A-16C to 19A-B) is 1 mm or longer, 2 mm or longer, 3 mm or longer, and 5 mm or longer. When the perforation/incision part is the plate-like blade 13 as shown in FIG. 2, the length of the perforation/incision target part along the perforation/incision part is 0.3 times or greater, 0.5 times or greater, 0.8 times or greater, and 1.0 times or greater than the length of the blade edge 131. When the length of the perforation/incision target part along the perforation/incision part is within the above range, in particular, the chromatography support is easily perforated or incised at the perforation/incision target part. Thus, the effects attained according to one or more embodiments of the present invention are exerted.

The number of the perforation/incision target part to be formed in a part of the chromatography support that comes into contact with the perforation/incision part is not particularly limited, provided that it is 1 or greater.

Feature of One or More Embodiments of the Present Invention

Subsequently, features of one or more embodiments of the present invention are described.

Figure 20A:
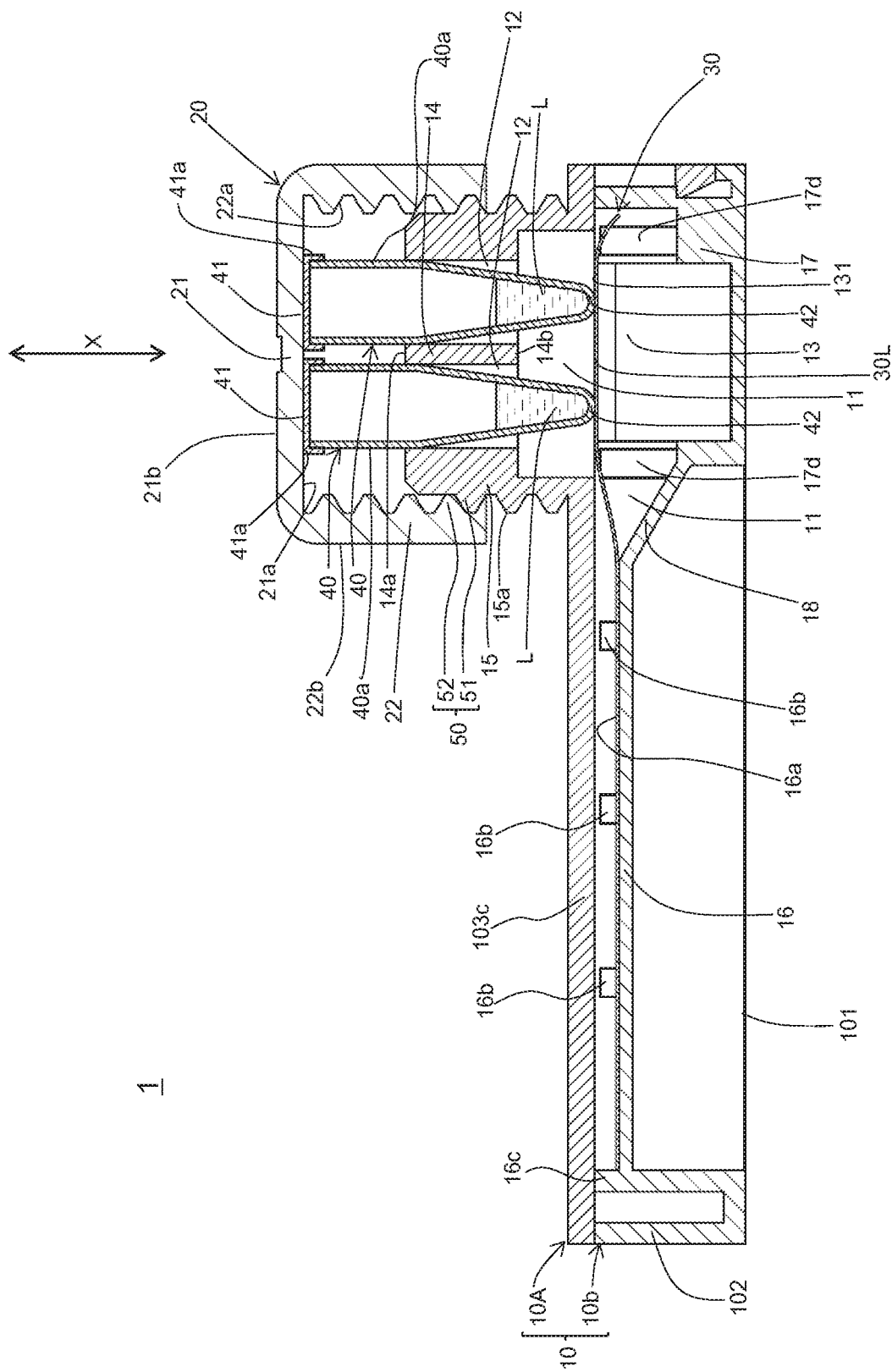
FIG. 20A schematically shows a cross section of the test device according to one or more embodiments of the present invention in a longitudinal direction in which the container is supported by the supporting part and positioned in the first position of the housing.
Figure 20B:
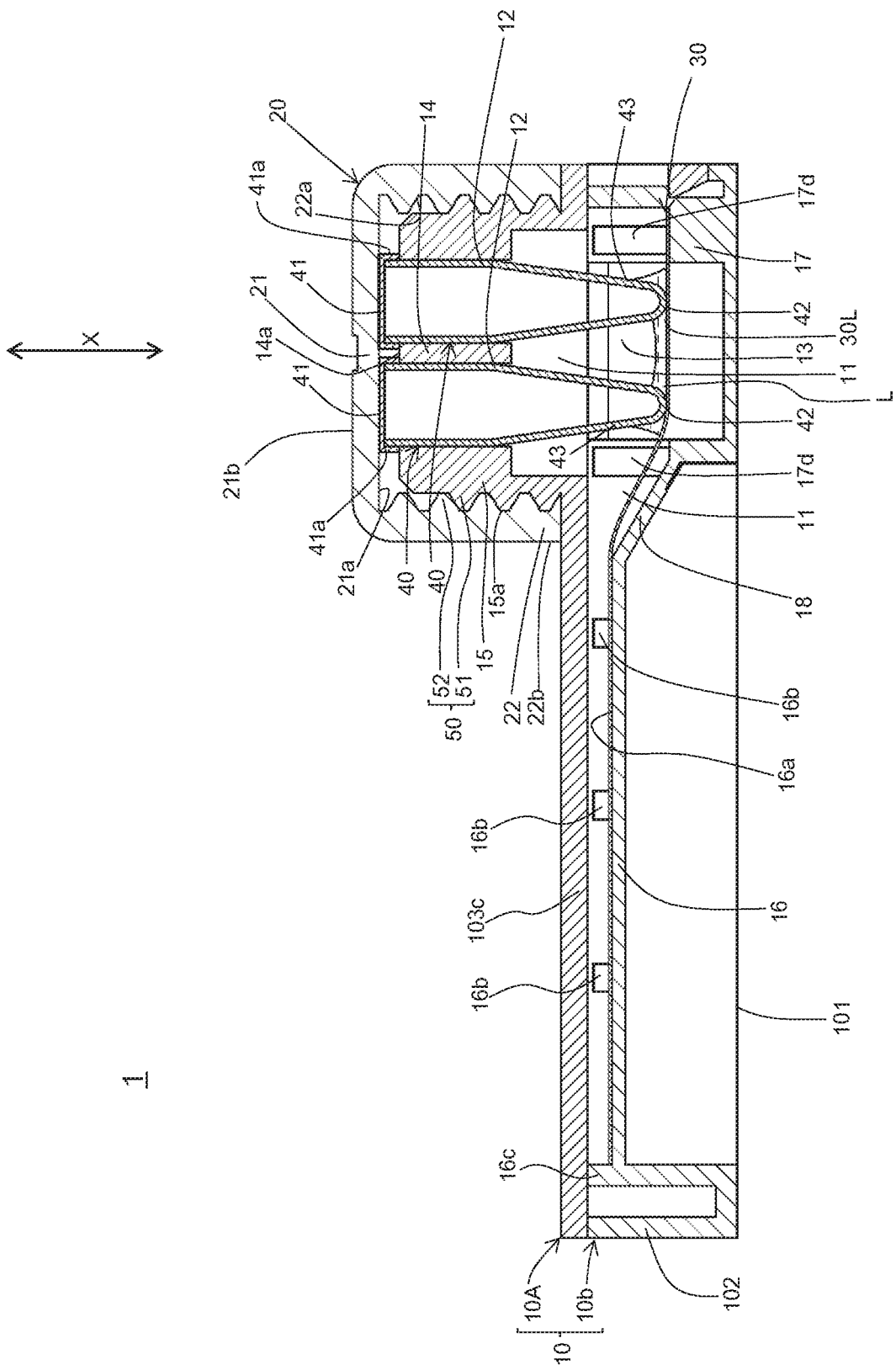
FIG. 20B schematically shows a cross section of the test device according to one or more embodiments of the present invention in a longitudinal direction in which the container is supported by the supporting part and positioned in the second position of the housing.

With reference to FIG. 20A to FIG. 20C, the mechanism of the test device 1 according to one or more embodiments of the present invention in which the containers 40 inserted into the holes 12 of the supporting part 14 and supported thereby are perforated or incised by the perforation/incision part 13 is described.

Figure 21A:
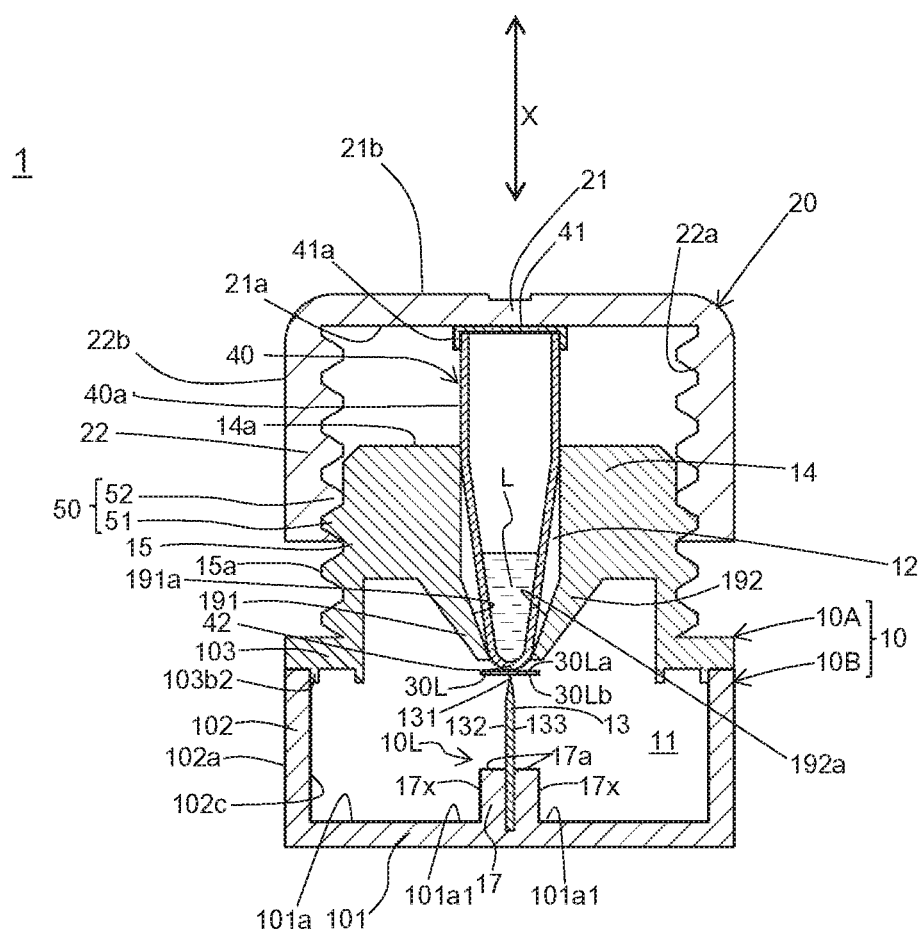
FIG. 21A schematically shows an end plane of the test device according to one or more embodiments of the present invention including a container in a short-width direction in which the container is supported by the supporting part and positioned in the first position of the housing.

FIG. 20A and FIG. 21A each show the containers 40 accommodating liquids L that are inserted into the holes 12 of the supporting part 14 and supported thereby. The inner end 42 of the container 40 faces the edge 131 of the blade 13. The position where the container is supported by the supporting part with one end of the container facing the perforation/incision part is defined as "the first position."

Figure 21B:
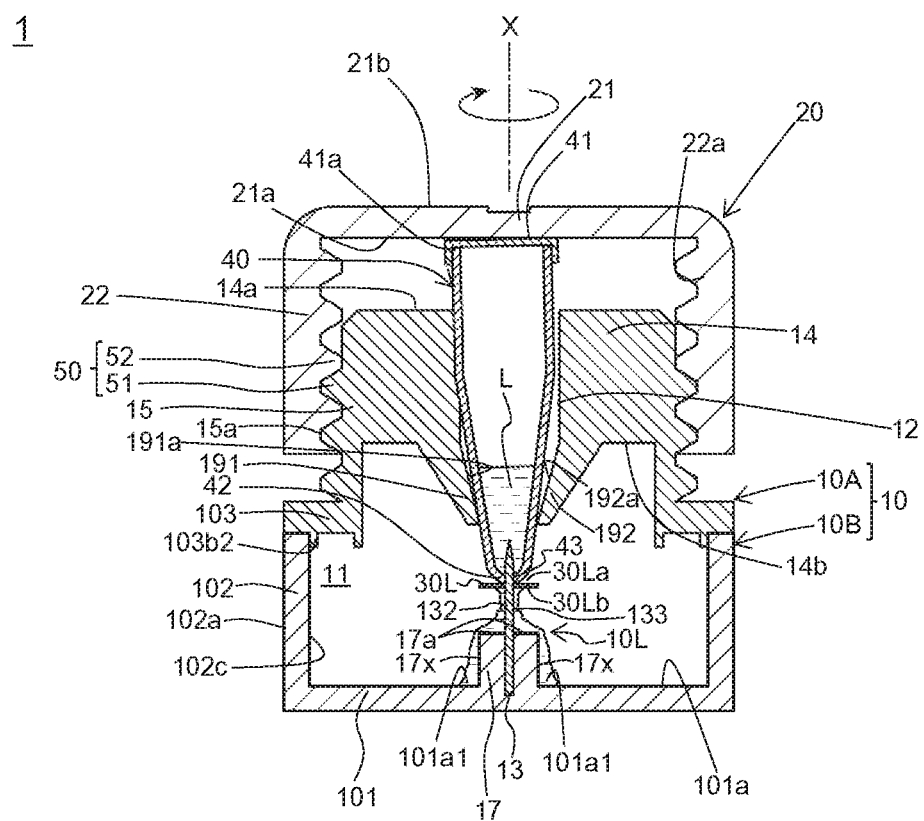
FIG. 21B schematically shows an end plane of the test device according to one or more embodiments of the present invention including a container in a short-width direction in which the container is supported by the supporting part and allowed to migrate from the first position to the second position of the housing.
Figure 21C:
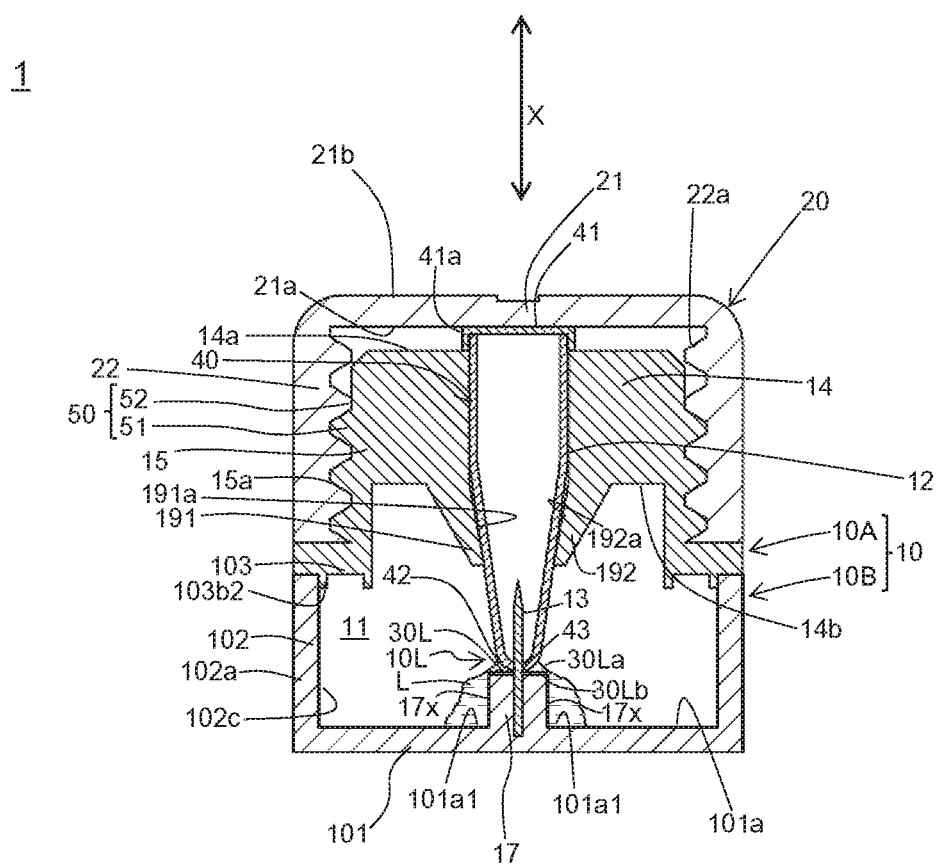
FIG. 21C schematically shows an end plane of the test device according to one or more embodiments of the present invention including a container in a short-width direction in which the container is supported by the supporting part and positioned in the second position of the housing.

FIG. 20B and FIG. 21C each show the containers 40 supported by the holes 12 of the supporting part 14 and positioned in the first position that are pushed toward the perforation/incision part 13 and allowed to completely migrate to the position where the inner ends 42 of the containers 40 abut against the fixing parts 17 of the housing 10. In this case, the containers 40 are incised by the blade 13 from the inner ends 42 of the containers 40. The position where the container is supported by the supporting part, guided by the container guide, and allowed to migrate to the position where the container is incised by the perforation/incision part is defined as "the second position." As shown in FIG. 20B and FIG. 21C, according to one or more embodiments, the container in the second position abuts against a part of the housing other than the perforation/incision part.

While the container 40 supported by the hole 12 of the supporting part 14 is guided from the first position to the second position, the container 40 is perforated or incised by the perforation/incision part 13, and liquid L accommodated in the container 40 leaks to the position where the liquid comes into contact with the liquid contact part 30L of the chromatography support 30. FIG. 21B schematically shows the container 40 while it migrates from the first position to the second position. The container 40 is perforated or incised by the perforation/incision part 13, and the leakage port 43 is then formed thereon. From the container 40 comprising the leakage port 43 formed thereon, the liquid L accommodated therein leaks through the leakage port 43 into the internal space 11, and the liquid comes into contact with a part of the housing comprising, in addition to the liquid contact part 30L of the chromatography support 30, the perforation/incision part 13 and the bottom wall 101 (the fixing part 17, in particular) in the vicinity of the liquid contact part 30L. An opening that is formed on the container when the container is perforated or incised by the perforation/incision part is referred to as a "leakage port" herein. When a blade serves as a perforation/incision part, in particular, a "leakage port" that is formed when the container is incised by the blade may be referred to as an "incision."

According to one or more embodiments, in addition, the liquid contact part 30L of the chromatography support 30 is accommodated in the housing 10 in a position between the supporting part 14 and the perforation/incision part 13, and the container 40 is perforated or incised by the perforation/incision part 13 together with the chromatography support 30. When the container 40 is in the first position, the inner end 42 of the container 40 faces the perforation/incision part 13 through the liquid contact part 30L of the chromatography support 30. When the container 40 supported by the supporting part 14 is guided to migrate from the first position to the second position, the container 40 is perforated or incised by the perforation/incision part 13 together with the liquid contact part 30L of the chromatography support 30. According to one or more embodiments, liquid L leaked from the container 40 easily comes into contact with the liquid contact part 30L of the chromatography support 30 and penetrates there through. The test device 1 provided with such features is capable of allowing the liquid L leaked from the container 40 to efficiently come into contact with the chromatography support 30.

According to one or more embodiments, as shown in FIG. 20A and FIG. 21A, the container 40 is supported by the supporting part 14 of the housing 10 and positioned in the first position, and the lid 20 is mounted on the lid-mounting part 15 surrounding the supporting part 14 of the housing 10. In this case, the housing-side screw-engagement part 51 on the outer peripheral surface 15a of the lid-mounting part 15 of the housing 10 is partially engaged with the lid-side screw-engagement part 52 on the inner peripheral surface 22a of the peripheral wall part 22 of the lid 20. Thus, the supporting part 14 of the housing 10 and the outer region 40a of the container 40 are covered by the lid 20. Subsequently, as shown in FIG. 21B, the lid 20 is allowed to revolve around an axis in a direction X in which the supporting part 14 of the housing 10 faces the lid 20, and the lid 20 is guided by the lid guide 50 to migrate toward the supporting part 14 of the housing 10 in the direction X. During migration, the main lid part 21 of the lid 20 abuts against the outer end 41 of the container 40, and the container 40 is pushed toward the perforation/incision part 13 to reach the second position shown in FIG. 20B and FIG. 21C. FIG. 21B schematically shows the container 40 pushed toward the perforation/incision part 13 with a slight inclination from the direction X as the lid 20 revolves. Thus, the leakage port 43 formed on the container 40 as a result of perforation or incision becomes open, liquid L efficiently leaks therefrom, and chromatography conditions can be stabilized.

According to one or more embodiments of the present invention, the test device does not necessarily comprise the lid. In such test device, for example, the container without a lid may be supported by the supporting part of the housing. A user pushes such container with fingers from the outside of the housing or operates an apparatus or the like from the outside. Thus, the container migrates from the first position to the second position.

In the test device according to one or more embodiments of the present invention, the surface of the housing and/or that of the chromatography support with which the liquid leaked from the container comes into contact have a water contact angle of 90 degrees or smaller. The term "water contact angle" used in one or more embodiments of the present invention refers to an angle at which water comes into contact with a surface of a substance. A water contact angle is measured by adding 1 µl of pure water dropwise to a target substance that was placed to maintain its surface flat and measuring a water contact angle of interest using a contact angle meter (MobileDrop, KRUSS). Measurement is performed to complete within 5 minutes after pure water is added dropwise at room temperature.

In one or more embodiments, a surface with which liquid L leaked from the container 40 comes into contact in the housing 10 is defined as "the liquid contact surface 10L." According to one or more embodiments, as described above, while the container 40 supported by the supporting part 14 is guided from the first position to the second position, the container 40 is perforated or incised by the perforation/incision part 13, the leakage port 43a is formed on the container 40, the liquid L accommodated in the container 40 leaks through the leakage port 43 into the internal space 11, and the liquid leaked from the container 40 comes into contact with the surfaces 30La and 30Lb of the liquid contact part 30L of the chromatography support 30 and the liquid contact surface 10L of the housing 10, as shown in FIG. 20B, FIG. 21B, and FIG. 21C. In one or more embodiments, specifically, the liquid contact surface 10L of the housing 10 encompasses the lateral surfaces 132 and 133 of the perforation/incision part 13, and a surface of a region adjacent to the perforation/incision part 13 on the bottom wall 101 (the upper surface 17a and the lateral surface 17x of the fixing part 17 and a region 101a1 in the vicinity of the fixing part 17 on the inner wall surface 101a of the bottom wall 101, in particular). When at least parts of the surfaces 30La and 30Lb of the liquid contact part 30L of the chromatography support 30 and the liquid contact surface 10L of the housing 10 have a water contact angle of 90 degrees or smaller, the liquid L leaked from the container sufficiently wets the surfaces. Thus, the leaked liquid L easily comes into contact with the chromatography support and it is sufficiently absorbed thereby. When the surfaces 30La and 30Lb of the liquid contact part 30L of the chromatography support 30 have a water contact angle of 90 degrees or smaller, specifically, the leaked liquid L is likely to be absorbed by the surfaces 30La and 30Lb of the liquid contact part 30L of the chromatography support 30 immediately. When the liquid contact surface 10L of the housing 10 has a water contact angle of 90 degrees or smaller, the leaked liquid L not immediately absorbed by the liquid contact part 30L of the chromatography support 30 can wet at least the liquid contact surface 10L of the housing 10 and remain in that site. Thus, such liquid is likely to be absorbed by the liquid contact part 30L of the chromatography support 30 with the elapse of time.

Figure 22:
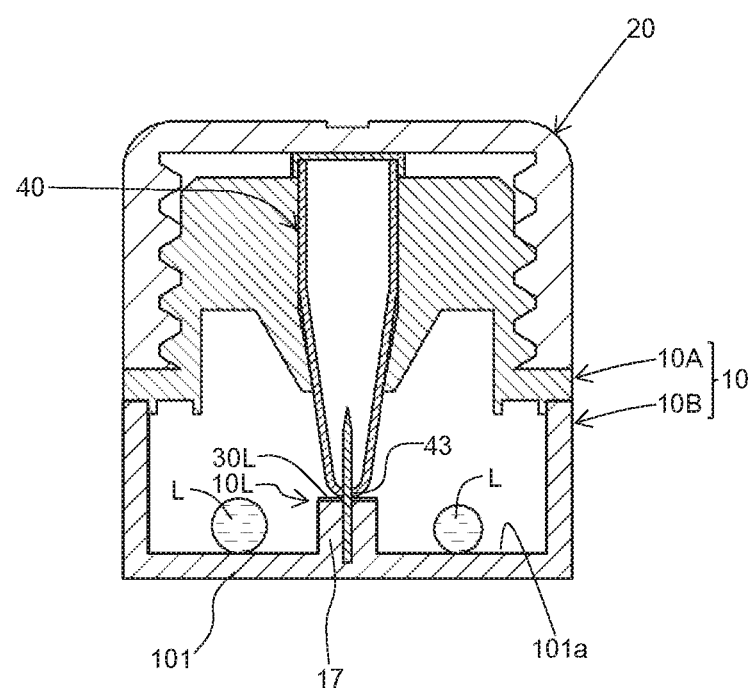
FIG. 22 schematically shows an end plane of a test device in which the surfaces of the housing and the chromatography support with which the liquid leaked from the container comes into contact have a water contact angle of 90 degrees or greater according to a comparative example including a container in a short-width direction in which the container is supported by the supporting part and positioned in the second position of the housing.

FIG. 22 schematically shows the container 40 supported by the supporting part 14 and guided from the first position to the second position using the test device 1" of a comparative example having the structure similar to that according to one or more embodiments described above, except that the surface of the housing 10 and that of the chromatography support 30 with which the liquid leaked from the container 40 comes into contact have a water contact angle exceeding 90 degrees. When the liquid L leaked from the leakage port 43 of the container 40 is not absorbed by the liquid contact part 30L of the chromatography support 30, the liquid L does not wet the liquid contact surface 10L of the housing 10, and forms droplets in the housing 10 as shown in the figure. With the use of the test device 1" of a comparative example, accordingly, the amount of the liquid L that comes into contact with the chromatography support 30 and is absorbed thereby is small. Thus, it is difficult to perform stable testing.

According to one or more embodiments of an aspect in which the lateral surfaces 132 and 133 of the perforation/incision part 13 of the housing 10 have a water contact angle of 90 degrees or smaller, as shown in FIG. 20B, FIG. 21B, and FIG. 21C, liquid L can smoothly leak from the container 40 through the leakage port 43 even if the perforation/incision part 13 is inserted into the leakage port 43 of the container 40 formed by the perforation/incision part 13. As a result, an intended amount of the liquid L can be smoothly supplied to the chromatography support 30.

On the surface of the housing and/or that of the chromatography support, a surface with a water contact angle of 90 degrees or smaller is formed by hydrophilic treatment. Examples of hydrophilic treatments include plasma treatment, fluorine gas treatment, coating with hydrophilic or water-soluble resin, such as polyvinyl pyrrolidone (PVP) or polyvinyl alcohol (PVA), surfactant coating, fine concave-convex processing, and combination of any thereof. A region including the surface of the housing and/or that of the chromatography support with which the liquid leaked from the container comes into contact may be constituted by a material comprising hydrophilic or water-soluble resin such as PVP or PVA. In particular, the liquid contact part of the chromatography support is constituted by a material comprising PVP or PVA.

EXAMPLES

Specific Examples of One or More Embodiments of the Present Invention

The test device 1 according to one or more embodiments of the present invention having the structure shown in FIG. 1A to FIG. 2 and FIG. 3A to FIG. 4C was prepared. The chromatography support 30 comprising a liquid receiver 31, a labeling agent holder 34, a detection part 32, and an absorption pad 33 provided on a substrate 35 having the structure shown in FIGS. 9A-9B were used.

As the container 40, a microtube for biochemical testing comprising an opening/closing part 41a at the outer end 41 of the housing 10 with the inner end 42 of the housing 10 being closed when it is supported by the supporting part 14 of the housing 10 of the test device 1 was used. When the container 40 was supported by the supporting part 14 of the test device 1, the length M in the guiding direction Y was 21.5 mm.

When the test device 1 was provided to adjust the guiding direction Y vertical, the container 40 was supported by the supporting part 14 of the housing 10 in a manner such that the inner end 42 of the container 40 would face downward in a vertical direction and the container 40 would be guided from the first position to the second position in that state, and the maximal length D (=B) in the guiding direction Y (=vertical direction V) of the incision 43 formed on the container 40 was 7.5 mm D/M was 0.349.

The test device 1 was provided to adjust the guiding direction Y vertical, and the container 40 accommodating 5 to 100 µl of a developing solution L for chromatography and the air in the remaining part therein was supported by the supporting part 14 of the housing 10 in a manner such that the inner end 42 would face downward in a vertical direction and the container 40 would be guided from the first position to the second position in that state. Thus, the developing solution L was allowed to leak and develop. When development of the developing solution L to the absorption pad 33 of the chromatography support 30 was observed 10 minutes after the container 40 had migrated to the second position, development was determined to be successful. The solution of the same amount was tested 20 times, and the number of successful development was recorded. The containers 40 each accommodating the developing solutions of relevant amounts were arranged in a vertical direction in a manner such that the inner ends 42 would face downward in a vertical direction. The results of measurements of the distance A from the inner end 42 to the liquid surface (i.e., the liquid level) and the rates of successful development are shown in the tables below. When the maximal length B (7.5 mm) of the incision 43 in the vertical direction was greater than the liquid level A, the rate of successful development was found to be 100%.

TABLE 1

| Amount of developing solution (µl) | 5 | 10 | 20 | 30 | 40 |
|---|---|---|---|---|---|
| Liquid level A (mm) | 2.0 | 3.0 | 4.5 | 5.5 | 6.5 |
| Frequency of successful development | 20/20 | 20/20 | 20/20 | 20/20 | 20/20 |
| Rate of successful development (%) | 100 | 100 | 100 | 100 | 100 |
| Amount of developing solution (µl) | 50 | 60 | 70 | 80 | 100 |
| Liquid level A (mm) | 7.0 | 7.5 | 8.8 | 9.1 | 10.0 |
| Frequency of successful development | 20/20 | 19/20 | 18/20 | 18/20 | 18/20 |
| Rate of successful development (%) | 100 | 95 | 90 | 90 | 90 |

Specific Examples of One or More Embodiments of the Present Invention

Figure 14A:
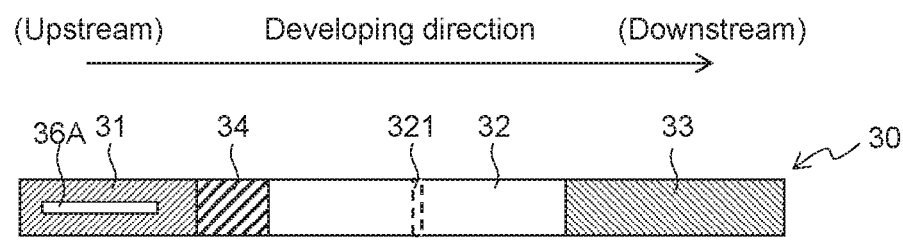
FIG. 14A-14B shows a structure of a chromatography support that can be used in one or more embodiments of the present invention. 14A shows a plane view, and 14B shows a lateral view.
Figure 14B:
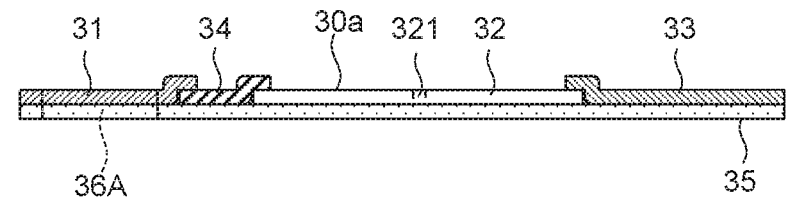
Figures 15A, 15B:
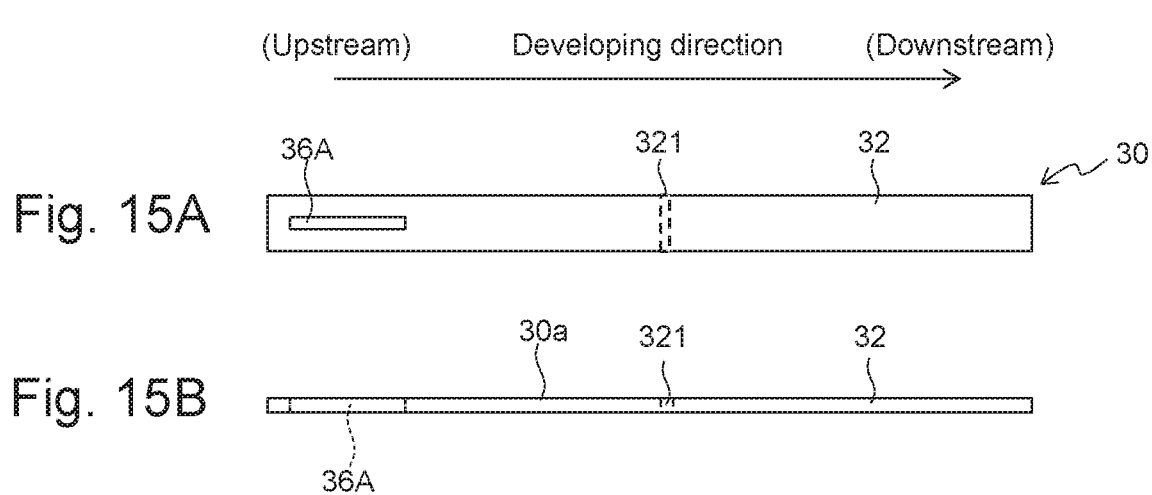
FIG. 15A-15B shows a structure of another chromatography support that can be used in one or more embodiments of the present invention. 15A shows a plane view, and 15B shows a lateral view.

The test device 1 according to one or more embodiments of the present invention having the structure shown in FIG. 1A to FIG. 2 and FIG. 11A to FIG. 12B was prepared. The chromatography support 30 (incision +) comprising a liquid receiver 31, a labeling agent holder 34, a detection part 32, and an absorption pad 33 provided on a substrate 35 having the structure shown in FIGS. 14A-14B, provided that an incision 36B with the length of 5 mm in the direction of development as shown in FIG. 16A was provided on the liquid receiver 31 instead of the slit hole 36A, was used. The chromatography support 30 (incision −) had the same structure as with the chromatography support 30 (incision +) except that the incision 36B was not formed.

As the container 40A-14B, a microtube for biochemical testing comprising an opening/closing part 41a at the outer end 41 of the housing 10 with the inner end 42 of the housing 10 being closed when it is supported by the supporting part 14 of the housing 10 of the test device 1 was used.

The container 40 accommodating 70 µl of a developing solution L for chromatography was supported by the supporting part 14 of the housing 10 of the test device 1, in a manner such that the inner end 42 would face downward in a vertical direction, and the container was pushed toward the blade 13 from the outer end 41 without the use of the lid 20. Thus, the container 40 was allowed to migrate from the first position to the second position, and the developing solution L was allowed to leak from the container 40 and develop in the chromatography support 30. In this case, the maximal force in the vertical direction required to push the container 40 (i.e., the maximal pushing force) was measured. Measurement was performed using the digital force gauges ZTA-200N (Imada Co., Ltd.) and the test stand HV-500N II (Imada Co., Ltd.). The "incision +" and the "incision −" were each subjected to measurement 10 times, and the mean and the standard deviation were determined. The results are shown in Table 2. It was confirmed that provision of the chromatography support 30 with the incision 36B would lower the maximal pushing force.

TABLE 2

| | Maximal pushing force (N) | | | | | |
|---|---|---|---|---|---|---|
| Incision+ | 22.34 | 25.97 | 17.05 | 14.11 | 24.30 | 24.01 |
| Incision− | 34.29 | 39.39 | 35.27 | 34.19 | 30.18 | 33.41 |

| | Maximal pushing force (N) | | | | Mean | Standard deviation |
|---|---|---|---|---|---|---|
| Incision+ | 22.74 | 25.28 | 23.72 | 19.80 | 21.93 | 3.82 |
| Incision− | 34.88 | 38.71 | 33.02 | 39.98 | 35.33 | 3.12 |

In the same manner as described above, the container 40 was supported by the supporting part 14 of the housing 10 and allowed to migrate from the first position to the second position, and whether or not the developing solution L had developed to the absorption pad 33 of the chromatography support 30 was evaluated 10 minutes after the container 40 had migrated to the second position. When the developing solution L had developed to the absorption pad 33, development was determined to be successful. The "incision +" and "incision −" were each subjected to testing 50 times, the number of successful development was recorded, and the rates of successful development were determined. The results are shown in Table 3. It was confirmed that provision of the chromatography support 30 with the incision 36B would enhance the rate of successful development.

TABLE 3

| | Frequency of successful development | Rate of successful development (%) |
|---|---|---|
| Incision + | 50/50 | 100 |
| Incision − | 45/50 | 90 |

Specific Examples of One or More Embodiments of the Present Invention

The test device 1 according to one or more embodiments of the present invention having the structure shown in FIG. 1A to FIG. 2 and FIG. 20A to FIG. 21C was prepared. The chromatography support 30 comprising a liquid receiver 31, a labeling agent holder 34, a detection part 32, and an absorption pad 33 provided on a substrate 35 having the structure shown in FIGS. 9A-9B was used. The surface of the liquid receiver 31 and the surface of the substrate 35 correspond to the surfaces 30La and 30Lb of the liquid contact part 30L. The blade 13 made of a metal was used, the blade 13 that was not treated with a rust-preventive water-repellent spray was designated to be "without an oil coating," and the blade 13 that was treated with a rust-preventive water-repellent spray was designated to be "with an oil coating." The housing 10 in which a main unit comprising the bottom wall 101, the side wall 102, and the upper wall 103 is made of a polycarbonate resin was used.

The water contact angles of the lateral surface (132 or 133) of the blade 13 with or without an oil coating, the surface of the fixing part 17 of the housing 10 (the upper surface 17a or lateral surface 17x), the surface of the liquid receiver 31 of the chromatography support 30, and the surface of the substrate 35 of the chromatography support 30 of the test device 1 were measured. The water contact angle was measured by adding 1 µl of pure water dropwise to a target substance that was placed to maintain its surface flat and measuring a water contact angle of interest using a contact angle meter (MobileDrop, KRUSS). Measurement was performed to complete within 5 minutes after pure water was added dropwise at room temperature. Measurement of the water contact angle was performed 3 times and the results shown below were obtained.

TABLE 4

| | Water contact angle (degrees) | | | Mean | Standard deviation |
|---|---|---|---|---|---|
| Blade (without oil coating) | 75.35 | 76.63 | 77.49 | 76.49 | 1.08 |
| Housing fixing part 17 | 84.86 | 82.56 | 83.61 | 83.68 | 1.15 |
| Support liquid receiver 31 | 0 | 0 | 0 | 0 | 0.00 |
| Support substrate 35 | 88.71 | 87.37 | 87.98 | 88.02 | 0.67 |
| Blade (with oil coating) | 123.53 | 135.36 | 141.27 | 133.39 | 9.03 |

0: Due to liquid impregnation

In the case of the test device 1 according to one or more embodiments described above using the blade 13 without an oil coating, a test solution adequately leaked from the container 40, and the leaked solution was absorbed by the chromatography support 30.

In the case of the test device 1 according to one or more embodiments described above using the blade 13 with an oil coating, a test solution did not adequately leak from the container 40 in some occasions.

DESCRIPTION OF NUMERAL REFERENCES

1: Test device
10: Housing
10L: Liquid contact surface of the housing
12: Hole (container guide)
13: Blade (perforation/incision part)
131: Blade edge
14: Supporting part
17: Fixing part
17b: Tapered end
17c3: Concave-convex surface
30: Chromatography support
30L: Liquid contact part of the chromatography support
36A, 36B, 36C, 36D, and 36E: Perforation/incision target part
40: Container
42: Internal end of the container 40 (one end)
43: Incision
L: Liquid
Y: Guiding direction
V: Vertical direction All publications, patents, and patent applications cited herein are incorporated herein by reference in their entirety.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. A test device comprising:
 a chromatography support; and
 a housing accommodating the chromatography support, wherein the housing comprises:
  a supporting part that supports a container accommodating a liquid used for chromatography, and
  a perforation/incision part that perforates or incises the container supported by the supporting part and the chromatography support to leak the liquid from the container to a position where the liquid comes into contact with the chromatography support, and
 wherein the chromatography support comprises, at a position that comes into contact with the perforation/incision part, a perforation/incision target part provided thereon in advance.

2. The test device according to claim 1,
 wherein
 the chromatography support is accommodated in the housing in a manner such that the perforation/incision target part of the chromatography support is positioned between the supporting part and the perforation/incision part, and
 the supporting part comprises a container guide that supports the container and guides the container from a first position where the container faces the perforation/incision part through the perforation/incision target part of the chromatography support to a second position where the container and the perforation/incision target part of the chromatography support are perforated or incised together by the perforation/incision part.

3. The test device according to claim 1,
 wherein
 the perforation/incision target part is one or more elements selected from the group consisting of:
  an incision that penetrates through the chromatography support in a thickness direction;
  a groove formed on a part of the chromatography support in a thickness direction;
  a hole that penetrates through the chromatography support in a thickness direction; and
  a line of perforation comprising two or more elements selected from among the incision that penetrates through the chromatography support in a thickness direction, the groove formed on a part of the chromatography support in a thickness direction, and the hole that penetrates through the chromatography support in a thickness direction.

4. The test device according to claim 1, wherein a length of the perforation/incision target part along the perforation/incision part is 1 mm or greater.

5. A test device comprising:
 a chromatography support; and
 a housing for accommodating the chromatography support,
 wherein the housing comprises:
  a supporting part that supports a container accommodating a liquid used for chromatography; and
  a perforation/incision part that perforates or incises the container supported by the supporting part to leak the liquid from the container to a position where the liquid comes into contact with the chromatography support, and
 wherein
 the chromatography support is accommodated in the housing in a manner such that a part of the chromatography support is positioned between the supporting part and the perforation/incision part, and
 the supporting part comprises a container guide that supports the container and guides the container from a first position where the container faces the perforation/incision part through the part of the chromatography support to a second position where the container and the part of the chromatography support are perforated or incised together by the perforation/incision part.

6. The test device according to claim 1,
 wherein
 the perforation/incision part is a blade with an edge provided thereon,
 the supporting part comprises a container guide that supports the container and guides the container from a first position where one end of the container faces the blade edge to a second position where the container is incised by the blade from the one end of the container, and
 when a length of the container supported by the supporting part in a direction guided by the container guide is designated "M," and
 a maximal length of an incision formed on the container in the guiding direction when the container is supported by the supporting part and guided from the first position to the second position is designated "D,"
 D/M is 0.2 or greater.

7. The test device according to claim 6,
 wherein
 the blade is a plate-like blade comprising the edge on one side and a base end on the other side,
 an inner wall surface of the housing comprises a fixing part that flanks the blade in a thickness direction to fix the base end of the blade formed thereon,
 the fixing part comprises a tapered end that makes a dimension of the fixing part in the thickness direction of the blade to become smaller toward the blade edge, and
 when the container is supported by the supporting part and guided from the first position to the second position, the tapered end of the fixing part is inserted into the incision formed on the container.

8. The test device according to claim 7, wherein the tapered end of the fixing part has a concave-convex surface that is protruded and/or recessed in the thickness direction of the blade.

9. The test device according to claim 1, wherein a surface of the housing and/or a surface of the chromatography support with which the liquid leaked from the container comes into contact has a water contact angle of 90 degrees or smaller.

10. The test device according to claim 9, wherein the surface of the housing and/or the surface of the chromatography support having a water contact angle of 90 degrees or smaller is treated by a hydrophilic treatment.

11. The test device according to claim 6,
 wherein
 the blade is a plate-like blade comprising the edge on one side and a base end on the other side, an inner wall surface of the housing comprises a fixing part that flanks the blade in a thickness direction to fix the base end of the blade formed thereon, the fixing part comprises a tapered end that makes a dimension of the fixing part in the thickness direction of the blade to become smaller toward the blade edge, and when the container is supported by the supporting part and guided from the first position to the second position, the tapered end of the fixing part is inserted into the incision formed on the container.

12. The test device according to claim 11, wherein the tapered end of the fixing part has a concave-convex surface that is protruded and/or recessed in the thickness direction of the blade.

* * * * *